United States Patent
Bogdahn et al.

(10) Patent No.: US 10,744,095 B2
(45) Date of Patent: Aug. 18, 2020

(54) PHARMACEUTICAL DOSAGE FORM FOR APPLICATION TO MUCOUS MEMBRANES

(71) Applicant: Universität Greifswald, Greifswald (DE)

(72) Inventors: Malte Bogdahn, Greifswald (DE);
Kirsten Kirsch, Greifswald (DE);
Michael Grimm, Greifswald (DE);
Mirko Koziolek, Greifswald (DE);
Werner Weitschies, Greifswald (DE)

(73) Assignee: Universität Greifswald, Greifswald (DE)

( * ) Notice: Subject to any disclaimer, the term of this patent is extended or adjusted under 35 U.S.C. 154(b) by 0 days.

(21) Appl. No.: 15/539,596

(22) PCT Filed: Dec. 22, 2015

(86) PCT No.: PCT/EP2015/002601
§ 371 (c)(1),
(2) Date: Jun. 23, 2017

(87) PCT Pub. No.: WO2016/102067
PCT Pub. Date: Jun. 30, 2016

(65) Prior Publication Data
US 2018/0036251 A1    Feb. 8, 2018

(30) Foreign Application Priority Data

Dec. 23, 2014 (DE) .......... 10 2014 119 576

(51) Int. Cl.
| | |
|---|---|
| A61K 9/70 | (2006.01) |
| A61K 9/00 | (2006.01) |
| A61K 9/48 | (2006.01) |
| A61K 31/196 | (2006.01) |
| A61M 31/00 | (2006.01) |
| A61K 45/06 | (2006.01) |
| A61J 7/00 | (2006.01) |
| A61K 31/56 | (2006.01) |
| A61K 31/58 | (2006.01) |
| A61K 47/32 | (2006.01) |

(52) U.S. Cl.
CPC .......... *A61K 9/4808* (2013.01); *A61J 7/0092* (2013.01); *A61K 9/006* (2013.01); *A61K 9/0031* (2013.01); *A61K 9/0034* (2013.01); *A61K 9/7007* (2013.01); *A61K 9/7069* (2013.01); *A61K 9/7084* (2013.01); *A61K 31/196* (2013.01); *A61K 31/56* (2013.01); *A61K 31/58* (2013.01); *A61K 45/06* (2013.01); *A61M 31/00* (2013.01); *A61M 31/002* (2013.01); *A61K 9/0036* (2013.01); *A61K 9/703* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 4,228,149 | A * | 10/1980 | Brewer | A61K 9/0068 424/438 |
| 5,330,761 | A * | 7/1994 | Baichwal | A61K 9/006 424/440 |
| 2004/0081699 | A1 | 4/2004 | Rademacher et al. | |
| 2005/0096673 | A1 * | 5/2005 | Stack | A61B 17/0469 606/151 |
| 2005/0175699 | A1 | 8/2005 | Cuine-Backert | |
| 2009/0123390 | A1 * | 5/2009 | Hill | A61K 9/006 424/45 |
| 2011/0091522 | A1 * | 4/2011 | Murwitz | A61K 9/009 424/440 |
| 2011/0174653 | A1 * | 7/2011 | Schwarz | A61J 3/071 206/461 |
| 2012/0226189 | A1 * | 9/2012 | Fitzgerald | A61B 10/02 600/562 |
| 2014/0335153 | A1 | 11/2014 | Allen | |
| 2016/0081670 | A1 * | 3/2016 | Lubinski | A61B 10/02 600/572 |

FOREIGN PATENT DOCUMENTS

| | | | | |
|---|---|---|---|---|
| EP | | 0202159 A2 * | 11/1986 | ........... A61K 9/0065 |
| EP | | 1 095 650 | 5/2001 | |
| WO | WO 2000/032171 | | 6/2000 | |
| WO | WO 2000/042992 | | 7/2000 | |
| WO | WO 2003/007913 | | 1/2003 | |
| WO | WO 2005/039499 | | 5/2005 | |
| WO | | 2007083309 A2 | 7/2007 | |
| WO | WO 2009/125432 | | 10/2009 | |
| WO | WO 2009/144558 | | 12/2009 | |
| WO | WO 2010/135053 | | 11/2010 | |

OTHER PUBLICATIONS

Batchelor, Pharmaceutical Research, 22(2), pp. 175-181. (Year: 2005).*
Search Report regarding Singaporean Application No. 11201705021Q, dated Feb. 2, 2018.
Cui et al., "Nanoparticles Incorporated in Bilaminated Films: a Smart Drug Delivery System for Oral Formations", Biomacromolecules, 2007, 8(9):2845-2850.

(Continued)

*Primary Examiner* — Abigail Vanhorn
(74) *Attorney, Agent, or Firm* — Dentons US LLP

(57) ABSTRACT

The present invention relates to a pharmaceutical dosage form for application to a mucous membrane, in particular to a buccal, intestinal, rectal or vaginal mucous membrane, comprising at least one sheet like, in particular film shaped, foil shaped or wafer shaped preparation comprising the active pharmaceutical ingredient, a release mechanism, and a trigger mechanism, wherein the trigger mechanism is adapted to trigger, at a predetermined site of action, in particular of the gastrointestinal tract, of the rectum or of the vagina, the release of the sheet like preparation by the release mechanism.

13 Claims, 8 Drawing Sheets

(56) References Cited

OTHER PUBLICATIONS

Eaimtrakarn et al., "Evaluation of Gastrointestinal Transit Characteristics of Oral Patch Preparation Using Caffeine as a Model Drug in Human Volunteers", Drug Metabol. Pharmacokin. (2002) 17(4):284-291.
Gupta et al., "Mucoadhesive intestinal devices for oral delivery of salmon calcitonin", Journal of Controlled Release, (2013) 172(3):753-762.
Gohel et al., "Modulation of Active Pharmaceutical material release from a novel 'tablet in capsule system' containing an effervescent blend", Journal of Controlled Release, (2002) 79(1-3):157-164.
Patel et al.,"Pulsatile drug delivery system for treatment of various inflammatory disorders:A Review", International Journal of Drug Development and Research (2012) 4(3):67-87.
Anonymous: "Applications of Pharmacokinetic Principles in Drug Development", Springer Science and Business Media, (2012), p. 183.
Office Action regarding Europe Application No. 112035P520PCEP dated Mar. 20, 2020.

\* cited by examiner

Fig. 5
a) Side view
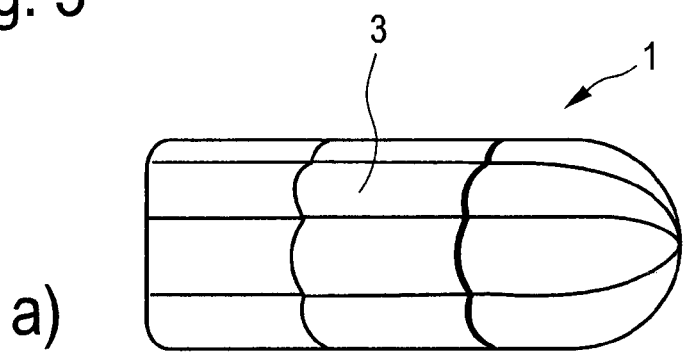
b) Front view
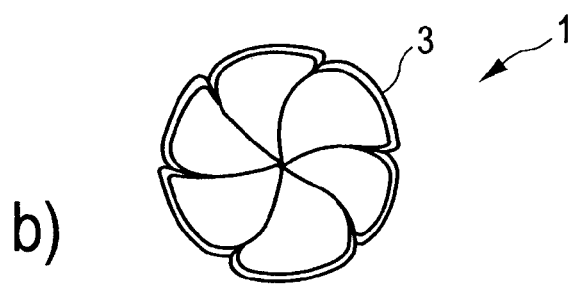
c) Photograph of the prototype
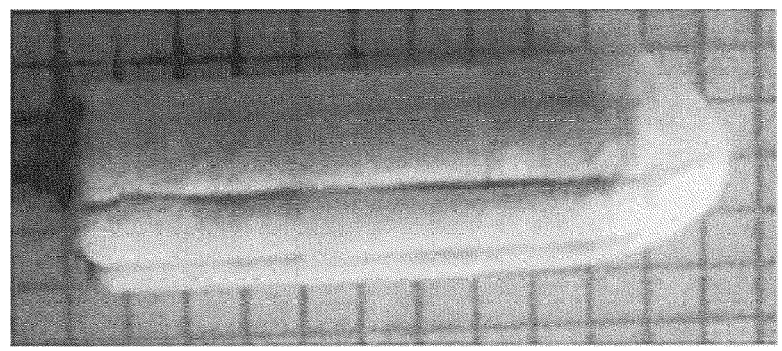

Fig. 6
Side view
a) 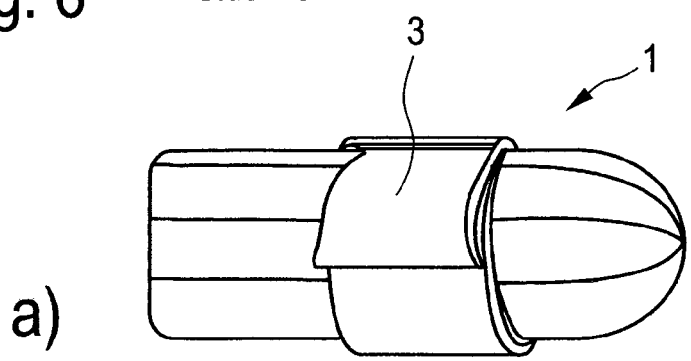
Front view
b) 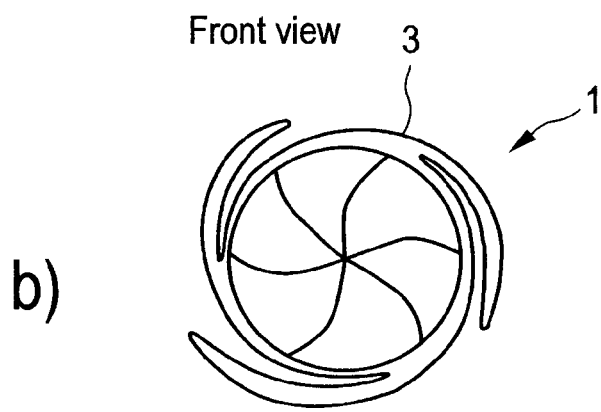
c) Photograph of the prototype
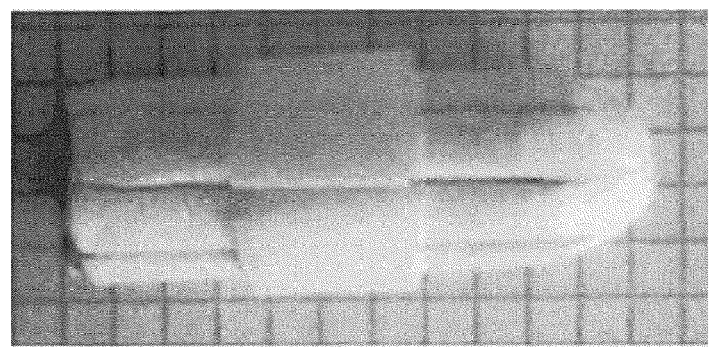

PHARMACEUTICAL DOSAGE FORM FOR APPLICATION TO MUCOUS MEMBRANES

CROSS-REFERENCE TO RELATED APPLICATIONS

This application is a 371 National Stage application of International Application No. PCT/EP2015/002601, filed Dec. 22, 2015, which claims the benefit of application No. 10 2014 119 576.0 DE, filed Dec. 23, 2014, and is herein incorporated by reference in its entirety.

FIELD OF THE INVENTION

The present invention relates to a pharmaceutical dosage form for application on a mucous membrane, in particular buccal, intestinal, rectal or vaginal mucosa.

The pharmaceutical dosage form is designed such that it comprises at least one sheet like, in particular film shaped, foil shaped or wafer shaped preparation comprising the active pharmaceutical ingredient, a release mechanism, and a trigger mechanism, wherein the trigger mechanism is adapted to trigger, at a predetermined site of action, in particular of the gastrointestinal tract, of the rectum or of the vagina, the release of the sheet like preparation by the release mechanism.

Thereby, inter alia, the bioavailability of the active pharmaceutical ingredient is advantageously increased by pressing the film shaped, foil shaped or wafer shaped preparation against the mucous membrane at the application site and thus achieving a controlled contact, a rapid uptake of the drug through the mucous membrane into the blood and thereby an increase in the bioavailability.

Especially the bioavailability is a pharmacological measure which is of great importance for the applicability of an active pharmaceutical ingredient and a dosage form comprising such an active pharmaceutical ingredient. Generally, the bioavailability indicates how rapidly and to what extent the active pharmaceutical ingredient is taken up respectively reabsorbed and is available at the site of action. For drugs that are administered intravenously the bioavailability is 100% by definition. The bioavailability observed after oral administration is generally called oral bioavailability.

DESCRIPTION OF THE RELATED ART

Numerous drugs are in particular unsuitable for oral administration, since they show a too small bioavailability and/or highly variable intra-individual plasma levels. Possible causes for this are the degeneration or deactivation of the drug by digestive secretions and enzymes, dilution effects by intestinal fluids, poor resorbability, a high first pass effect and a very short length of stay at the absorption window. Among these drugs are, for example, proteins and peptides such as Insulin, Buserelin, Oesmopressin, Calcitonin, and Estrogen as well as biotechnologically produced drugs such as antibodies, e.g. Rituximab.

There are numerous efforts to study the properties of various mucous membranes of mammals, especially humans, and to improve the bioavailability of active pharmaceutical ingredients. The particular focus here are the properties of different mammalian, especially human, mucous membranes with respect to permeability for and influence of the drug absorption.

These study results suggest that the permeability of mucous membranes for different drugs increases in the following order: intestinal mucosa<colonic mucosa<buccal mucosa-vaginal mucosa (Alam, M. A. et al., "*Everted gut sac model as a tool in pharmaceutical research: limitations and applications*", Journal of Pharmacy and Pharmacology, 2011, Vol. 64, pages 326-336; Berginc, K. et al., "*Development and Evaluation of an In Vitro Vaginal Model for Assessment of Drug's Biopharmaceutical Properties: Curcumin*", AAPS PharmSciTech, Vol. 13, No. 4, 2012, pages 1045-1053; van der Bijl, P. et al., "*Comparative in vitro permeability of human vaginal, small intestinal and colonic mucosa*", International Journal of Pharmaceutics, 2003, Vol. 261, pages 147-152; van der Bijl, P. et al., "*Penetration of human vaginal and buccal mucosa by 4.4-kd and 12-kd fluorescein-isothiocyanatelabeled dextrans*", Oral surgery oral medicine oral pathology, 1998, Vol. 85, No. 6, pages 686-691; Hosoya, K. et al., "*The structural Barrier of absorptive Mucosae: Site Difference of the Permeability of Fluorescein labeled Dextran in Rabbits*", Biopharmaceutics & Drug Disposition, 1993, Vol. 14, pages 685-696).

Furthermore, research results show that the concentrated application of an active pharmaceuticalingredient directly on the mucous membrane may increase its bioavailability compared to the administration of a solution or pill (Gupta. V. et al. "*Mucoadhesive intestinal devices for oral delivery of salmon calcitonin*", Journal of Controlled Release, 2013, Vol. 172, Issue 3, pages 753-762; Teutonico, D. et al. "*Concentration and surface of absorption: Concepts and applications to gastrointestinal patch delivery*", International Journal of Pharmaceutics, 2011, Vol. 413, pages 87-92).

BRIEF SUMMARY OF THE INVENTION

Such a concentrated application of an active pharmaceutical ingredient directly onto the mucous membrane can be achieved with dosage forms which contain the active pharmaceutical ingredient in a sheet like, in particular film shaped, foil shaped or wafer shaped preparation, in particular as a so-called wafer. Drawbacks of conventional wafers are, particularly, that known wafers dissolve partially or completely before the site of action and in particular for e.g. intestinal, rectal or vaginal wafers no contact with the mucous membrane can be guaranteed. Moreover, for e.g. intestinal, rectal and vaginal multilayered wafers no contact with the correct site of the wafer and in particular no sufficiently long contact with the mucous membrane can be guaranteed.

It is an object of the present invention to provide a pharmaceutical dosage form that overcomes the aforementioned drawbacks.

It is a further object of the present invention to provide a pharmaceutical dosage form that enhances the bioavailability of active pharmaceutical ingredients contained in dosage forms which are administered, in particular orally, vaginally or rectally.

It is yet a further object of the present invention to provide a pharmaceutical dosage form, in particular a dosage form containing the active pharmaceutical ingredient in a sheet like, in particular film shaped, foil shaped or wafer shaped, preparation, preferably a wafer, in which a release of the active pharmaceutical ingredient at its predetermined site of action is achieved and the amount of the active pharmaceutical ingredient available for resorption is increased, and/or an enhanced bioavailability and/or an enhanced rate of resorption is achieved.

In particular, it is an object of the present invention to provide a rapidly releasing dosage form with a systemic effect. Finally, it is yet a further object of the invention to provide a dosage form that makes it possible to apply active pharmaceutical ingredients, which cannot be administered orally due to poor bioavailability, at a predetermined site of action.

BRIEF DESCRIPTION OF THE SEVERAL VIEWS OF THE DRAWINGS

FIG. 5A-C show a schematic perspective illustration of a pharmaceutical dosage form according to the invention in accordance with a third embodiment of the invention in an initial state (FIG. 5A and FIG. 5B) and a photograph of a pharmaceutical dosage form according to the invention in accordance with the third embodiment of the invention in an initial state (FIG. 5C).

FIG. 6A-C show a schematic perspective illustration of a pharmaceutical dosage form according to the invention in accordance with a fourth embodiment of the invention in an initial state (FIG. 6A and FIG. 6B) and a photograph of a pharmaceutical dosage form according to the invention in accordance with the fourth embodiment of the invention in an initial state (FIG. 6C).

DETAILED DESCRIPTION OF THE INVENTION

Figure 1:
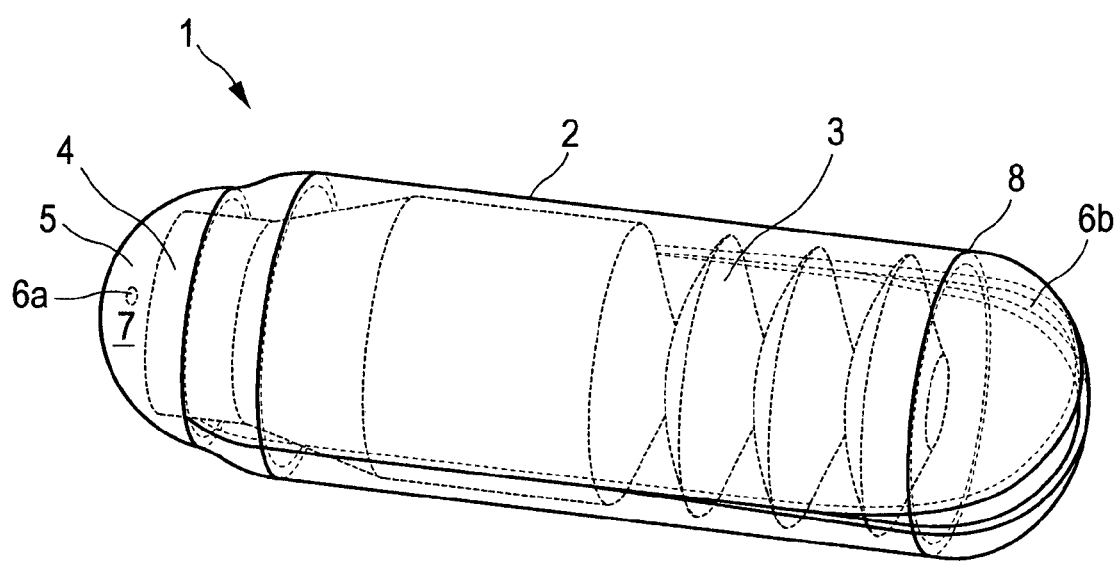
FIG. 1 shows a schematic perspective illustration of a pharmaceutical dosage form according to the invention in accordance with a first embodiment of the invention in an initial state.

Especially, the present invention relates to a pharmaceutical dosage form for the application, preferably to an upper gastrointestinal tract such as throat, esophagus, cardia and/or stomach, and particularly to the respective mucous membranes, that enables a local drug therapy and/or diagnostic investigation. Local diseases, in particular diseases of the esophagus, can be treated with local acting drugs. However, generally current pharmaceutical dosage forms or application systems often do not target the specific diseased location; particularly they do not target the esophagus and/or its mucous membrane. Therefore, generally a large amount of the applied drug, particularly the active pharmaceutical ingredient, is absorbed systemically, which may cause side effects, in particular adverse reactions. In particular, it is therefore an object of the present invention to improve the local application of a drug, particularly an active pharmaceutical ingredient. Preferably, certain embodiments according to the present invention specifically achieve and/or only aim for this object of the present invention. Moreover, certain embodiments according to the present invention may achieve further objects of the present invention. Furthermore, certain embodiments of the present invention may have the object to increase the bioavailability of an active pharmaceutical ingredient, locally deliver a useful substance, preferably a drug such as an active pharmaceutical ingredient, treat the esophagus with a local acting drug and/or reduce side effects, in particular adverse reactions.

These and other objects of the invention are achieved by the subject-matters of the present independent claims. Preferred embodiments are subject of the dependent claims.

In particular, the present inventors make use in an advantageous manner of the different permeability of various mucous membranes and particularly their suitability for taking up various drugs, which are inter alia different in their molecular size and lipophilicity, to provide a dosage form which allows a direct contact of the dosage form with the mucous membrane after the release at a predetermined site of action.

In particular, the present invention is a pharmaceutical dosage form for the application to mucous membrane, in particular to a buccal, intestinal, rectal or vaginal mucous membrane, and comprises at least one sheet-like, in particular film-shaped, foil-shaped or wafer-shaped, preparation comprising the active pharmaceutical ingredient, a release mechanism, and a trigger mechanism, wherein the trigger mechanism is adapted to trigger, at a predetermined site of action, in particular of the gastrointestinal tract, of the rectum or of the vagina, the release of the sheet-like preparation by the release mechanism.

Such a pharmaceutical dosage form according to the present invention advantageously allows improving the bioavailability of active pharmaceutical ingredients which are, in particular, contained in orally, vaginally, or rectally administered drugs, at a predetermined site of action. In addition, a release of the active pharmaceutical ingredient at its predetermined site of action is achieved by the pharmaceutical dosage form according to the present invention, whereby, in particular, the amount of the active pharmaceutical ingredient available for resorption can be increased as well as an increased bioavailability and an increased resorption rate can be achieved.

In particular, this is achieved with the dosage form according to the present invention by the fact that a dosage form according to the present invention rapidly releases a sheet-like, in particular film-shaped, foil-shaped, or wafer-shaped, preparation comprising the active pharmaceutical ingredient at a predetermined site of action with a systemic effect. Furthermore, the dosage form according to the present invention makes it possible to apply active pharmaceutical ingredients, which cannot be administered orally due to poor bioavailability, at a predetermined site of action.

Preferably the predetermined site of action is a mucous membrane, in particular a buccal, intestinal, rectal or vaginal mucous membrane.

The pharmaceutical dosage form according to the invention thus allows advantageously a coming into contact, in particular a direct contact, with the predetermined site of action, in particular a mucous membrane, preferably a tissue absorbing the active pharmaceutical ingredient, and further advantageously an uptake of the drug into the blood. The embodiment of the preparation comprising the active pharmaceutical ingredient is a sheet-like, in particular film-shaped, foil-shaped, or wafer-shaped preparation, in particular a so-called wafer, advantageously allows a release of the sheet-like preparation directly onto a mucous membrane and a coming into contact, preferably coming into contact with a relatively large surface area, at the predetermined site of release, respectively site of action, whereupon the sheet-like preparation can dissolve and release the active pharmaceutical ingredient. Such a coming into contact with the predetermined site of action advantageously allows an enhanced resorption of the active pharmaceutical ingredient, in particular a resorption of the active pharmaceutical ingredient to the mucous membrane, and the amount of the active pharmaceutical ingredient available for resorption is thereby increased. An increased bioavailability and/or an increased rate of absorption are thereby achieved, too.

Advantageously, an intestinal first-pass effect, i.e. a conversation of the active pharmaceutical ingredient during its first passage through the intestinal mucosa and possibly also through the liver, in particular of an orally administered dosage form, can be reduced by a pharmaceutical dosage form according to the invention. Also, the destruction of the active pharmaceutical ingredient before it reaches a predetermined site of action, e.g. by gastric acid and/or digestive enzymes, can be advantageously reduced by a pharmaceutical dosage form according to the invention. The bioavailability of the active pharmaceutical ingredient is also advantageously increased by a pharmaceutical dosage form according to the invention. A pharmaceutical dosage form according to the invention particular advantageously allows a reduction in dose maintaining approximately an equal therapeutic effect, especially when compared to an application of a comparable conventional preparation, such as tablets, solutions, vaginal creams or suppositories. Furthermore, a pharmaceutical dosage form according to the invention advantageously allows a more accurate dosing of the active pharmaceutical ingredient as well as, where necessary, a reduction of side effects, especially gastrointestinal side effects. The pharmaceutical dosage form according to the invention further advantageously allows a relatively simple and discrete handling as well as a simple, particularly space-saving storage, wherein active pharmaceutical ingredients, which are comprised in the pharmaceutical dosage form according to the invention, may have an improved stability, e.g. at high heat and humidity, in particular compared to solutions and gels.

The combination of a sheet-like preparation comprising the active pharmaceutical ingredient with a trigger mechanism and a release mechanism realized by the present invention advantageously supports the positive properties of a sheet-like preparation, particularly of a wafer.

At a predetermined trigger site that is equal to or different from the site of action the trigger mechanism triggers, e.g. by a key stimulus, the release mechanism and thereby the release of the sheet-like preparation at the site of action. For example, a release mechanism will expand and release the sheet-like preparation from the shell after the trigger mechanism triggers the release mechanism, e.g. by contacting with a key stimulus, for example depending on a change in pH value, pressure change or change of the fluid.

It is to be understood that the terms "site of action" and "application site" as used herein are used interchangeably. In this regard, it is also to be understood that "site of action" and "site of application" refer to the predetermined location of release of the preparation. Also it should be understood that an active pharmaceutical ingredient, which is released at the "site of action" respectively "application site" may exert its actual biochemical effect also at another location of the body or at another site of a biochemical cycle, e.g. at or after metabolization by the liver or reaching of an antibody at its target molecule. "Site of action" and "application site" as used herein do not necessarily refer to the location of the biochemical, medical effect of the active pharmaceutical ingredient.

A pharmaceutical dosage form according to the present invention particular advantageously allows to protect the sheet-like preparation, in particular wafer, until it reaches the predetermined site of action, respectively application site, and to bring the sheet-like preparation, respectively the wafer, into contact with the predetermined site of action, in particular with a mucous membrane.

The pharmaceutical dosage form according to the present invention thus allows a targeted and complete adhesion to the predetermined site of action, respectively application site.

Further, this advantageously allows, inter alia, a prolongation of the residence time at the absorption window, a displacement of fluids which could lead to an early detachment or dissolution of the sheet-like preparation, particularly of the wafer.

In a preferred embodiment of the pharmaceutical dosage form according to the present invention the pharmaceutical dosage form further comprises a shell, wherein the shell contains the at least one sheet-like, in particular film-shaped, foil-shaped, or wafer-shaped preparation comprising the active pharmaceutical ingredient, and wherein preferably the shell or the trigger mechanism comprises at least one aperture through which a fluid surrounding shell can come into contact with the inner space of the shell, wherein preferably the aperture is formed as a slit and/or the aperture is at least partially covered by the trigger mechanism.

In particular, the shell of the preparation makes it possible to protect the preparation by the shell against an unwanted release.

It is to be understood that a pharmaceutical dosage form according to the invention may comprise a shell which contains at least one or more sheet-like preparations comprising the active pharmaceutical ingredient. The shell of the pharmaceutical dosage form according to the invention and/or the dosage form itself further comprises a release mechanism and/or a trigger mechanism, wherein the trigger mechanism is adapted to trigger, at a predetermined site of action, in particular of the gastrointestinal tract, the release of the sheet-like preparation by the release mechanism.

The release of the sheet-like preparation by the release mechanism preferably takes place by at least partially moving out the preparation from at least a part of the shell.

An aperture in the shell allows in a particular advantageous manner an entry and/or a coming into contact of the fluid surrounding the shell, in particular of the fluid at the predetermined trigger site, e.g. a fluid of the gastrointestinal tract, into respectively with the inner space of the shell, in particular with the trigger mechanism and/or release mechanism which is located in the inner space of the shell.

In a preferred embodiment of the pharmaceutical dosage form according to the present invention the aperture is formed as a slit.

Such a slit may be embodied in different arrangements and configurations. For example, such a slit may be completely or partially circumferentially arranged at the shell. A slit that is completely circumferentially arranged at the shell may be arranged such that the slit divides the shell into multiple, in particular two parts.

An aperture according to the present invention, in particular a slit, may also be arranged such that the sheet-like preparation is released from the shell through the aperture, in particular slit, upon release of the sheet-like preparation.

In a preferred embodiment of the pharmaceutical dosage form according to the present invention the aperture can be covered by the trigger mechanism at least partially or completely.

Preferably the trigger mechanism covers the aperture at least partially or completely and thus allows to control, in particular to avoid the unwanted entry of fluid surrounding the shell.

In a preferred embodiment of the pharmaceutical dosage form according to the present invention the trigger mechanism is adapted to trigger the release of the sheet like preparation by the release mechanism after contacting the pharmaceutical dosage form, in particular the trigger mechanism, with a key stimulus.

The term "key stimulus" as used herein preferably refers to a change of state of the environment of the pharmaceutical dosage form according to the invention which is suitable to trigger the trigger mechanism. Such a change of state of the environment, which is suitable to trigger the trigger mechanism, is preferably a change that specifically occurs at the predetermined site of action, e.g. in the gastrointestinal tract. Such a change of state of the environment may be a predetermined change of a physical or chemical parameter of the environment of the dosage form. For example, at a predetermined site of action, preferably the gastrointestinal tract, a pressure or pH value that is specific for the predetermined site of action or a composition of the environment, e.g. a fluid at this site of action, that is specific for the predetermined site of action and in particular a change of it can serve as a key stimulus. E.g., a substantially lower pH value in the stomach as compared to the usual pH value in the neck area, the oral cavity and the pharyngeal cavity, and in particular the change of the pH value from the neck area, the oral cavity and the pharyngeal cavity to the stomach, can serve as a key stimulus.

In particular, a fluid surrounding the dosage form at the predetermined site of action, e.g. gastric juice and/or another fluid of the gastrointestinal tract or vaginal fluid at the predetermined site of action, can comprise a predetermined pH value, a predetermined pressure or a predetermined composition respectively a change of it that is suitable to trigger the trigger mechanism.

In a preferred embodiment of the pharmaceutical dosage form according to the present invention the trigger mechanism is adapted to trigger the release of the sheet like preparation by the release mechanism in a time controlled manner or immediately and/or the trigger mechanism is adapted to release the sheet like preparation in a time controlled manner or immediately after triggering of the trigger mechanism.

It is to be understood that a key stimulus that is adapted to trigger the trigger mechanism at a predetermined trigger site may trigger the trigger mechanism immediately or delayed, in particular time controlled, such that the trigger mechanism is adapted to trigger the release of the sheet like preparation by the release mechanism immediately or delayed such that the release occurs at the predetermined site of action, in particular of the gastrointestinal tract, the vagina or the rectum. The release mechanism may also be configured in such a way that this release mechanism can release the sheet like preparation immediately or delayed, in particular time controlled, at the predetermined site of action after triggering of the trigger mechanism.

In a particularly preferred embodiment of the pharmaceutical dosage form according to the present invention the trigger mechanism is adapted to trigger the release of the sheet like preparation by the release mechanism immediately and/or relatively quickly and/or the release mechanism is adapted to release the sheet like preparation immediately and/or relatively quickly after triggering the trigger mechanism.

In a preferred embodiment of the pharmaceutical dosage form according to the present invention a key stimulus for triggering the trigger mechanism involves a predetermined change of a physical or chemical parameter of a fluid surrounding the dosage form, in particular at a predetermined trigger site, preferably of the gastrointestinal tract, of the rectum or of the vagina, wherein the key stimulus is preferably selected from the group comprising a predetermined change of a pH value, a predetermined change of a pressure or a predetermined change of a composition of a fluid surrounding the dosage form.

A key stimulus may be chosen such that it acts on the trigger mechanism immediately at the predetermined site of action or already before reaching the predetermined site of action at a predetermined trigger site that is different from the site of action. The key stimulus may trigger the trigger mechanism immediately or delayed, it may in particular trigger the trigger mechanism in time controlled manner. The release of the release mechanism may occur immediately or delayed, in particular time controlled, after the triggering of the trigger mechanism. In particular, a delayed triggering of the trigger mechanism, particularly a time controlled triggering of the trigger mechanism, can be effected already at the removal of the dosage form from the packaging at the oral, rectal or vaginal intake of the dosage form, at the entry into or exit from a predetermined compartment of the gastrointestinal tract, particularly of the rectum or of the vagina, by reaching a predetermined temperature, a pH value of the surrounding medium or at the presence or absence of specific substances in the medium surrounding the dosage form. Alternatively, the triggering of the trigger mechanism at the oral intake of the dosage form, at the entry into or the exit from a predetermined compartment of the gastrointestinal tract, of the rectum or of the vagina, reaching a predetermined temperature or a pH value of the surrounding medium or the presence or absence of specific substances in the medium surrounding the dosage form may cause an immediate and/or relatively quick triggering of the trigger mechanism.

An immediate and/or relatively fast triggering of the trigger mechanism and/or an immediate and/or relatively rapid release of the release mechanism maybe advantageous to bring the sheet like preparation into contact with the site of action, in particular a mucous membrane, to make a contact with a relatively large surface area and/or to provide an advantageously increased surface area for the resorption of the active pharmaceutical ingredient at the site of action.

In a preferred embodiment of the pharmaceutical dosage form according to the present invention the trigger mechanism comprises a substance whose solubility and/or solidity depends on at least physical and/or chemical parameter of a fluid surrounding the dosage form, preferably selected from the group comprising a pH value, a pressure or a composition of a fluid surrounding the dosage form.

Preferably, the trigger mechanism is configured such that its physical and/or chemical properties, e.g. its geometry, and/or of aggregation, is changed by a key stimulus as described herein such that it can trigger the release of the sheet like preparation by the release mechanism at the predetermined site of action. The change of the properties of the trigger mechanism may occur immediately or delayed, in particular time controlled, or dynamically following the key stimulus at the predetermined trigger site.

The change of properties of the trigger mechanism may trigger an immediate or a delayed, in particular time controlled, or dynamic release of the sheet like preparation at the site of action. Under the term "dynamic" as used herein it is preferably to be understood that there is an adapted response to the conditions that are present at the trigger site and/or site of action, e.g. in the gastrointestinal tract. In other words, this refers to, for example, a principle which utilizes that the intestinal contents remains acid whereby a trigger mechanism is not (yet) triggered and thus a release mechanism does not release.

The term "time controlled" as used herein refers preferably to a predetermined time. For example, the release occurs after a predetermined period in case of a time controlled release.

It is also in the scope of the present invention that the release of the release mechanism occurs immediately after the triggering of the trigger mechanism. Alternatively, the release of the release mechanism may take place with a time delay which may be predetermined or which may dynamically change after the triggering of the trigger mechanism.

The change of the properties of the trigger mechanism may be caused by swelling, dissolution or changes in the solidity of the trigger mechanism or of a part thereof.

In this context it is to be understood that the trigger mechanism immediately or delayed, in particular time controlled or dynamically, e.g. after a predetermined period of time, triggers the release of the sheet like preparation by the release mechanism subsequently after the key stimulus. For example, a trigger mechanism may unblock the mobility of other elements, e.g. of the release mechanism, of the dosage form, or apertures which control the entry of a liquid surrounding a shell into the inner space of the shell, e.g. of the gastrointestinal tract or of the vagina, subsequently after the key stimulus.

In a preferred embodiment of the pharmaceutical dosage form according to the present invention the trigger mechanism is a coating, which preferably at least partially covers an aperture and/or a release mechanism or a part thereof.

In particular, in a preferred embodiment of the pharmaceutical dosage form according to the present invention the dosage form is provided a tampon for the vaginal application, wherein the tampon is at least partially wrapped, coated and/or embraced by a sheet like, in particular film shaped, foil shaped or wafer shaped, preparation comprising the active pharmaceutical ingredient. This tampon may advantageously serve as a trigger mechanism and e.g. swell when the tampon comes into contact with the vaginal fluid as a key stimulus and may trigger by the resulting expansion of the circumference or diameter of the tampon the release of the sheet like preparation by the release mechanism. In particular, such a release may establish a contact of the sheet like, in particular film shaped, foil shaped or wafer shaped, preparation comprising the active pharmaceutical ingredient with a predetermined site of action, in particular with a mucous membrane of the vagina, where the sheet like preparation rests against the vaginal mucous membrane. Additionally or alternatively, such a tampon dosage form may be at least partially coated by an (additional) trigger mechanism and/or a shell, in particular in form of a coating.

In particular, a trigger mechanism that covers an aperture and/or a release mechanism or a part thereof, at least partially or completely, can be arranged and/or adapted such that the trigger mechanism loosens, dissolves or swells subsequently after the key stimulus, and thus preferably triggers the release of the sheet like preparation.

In particular, an aperture respectively a slit can be sealed respectively covered by a trigger mechanism embodied as a cladding in such a way that an entry of fluid into the dosage form, preferably into an inner space of a shell, is avoided, wherein such a trigger mechanism may dissolve following a key stimulus at a predetermined trigger site and/or may rupture upon the release of the sheet like preparation at a predetermined site of action. Regarding its mechanical properties such a cladding is preferably adapted in such a way that it is not soluble in the fluids surrounding the dosage form, e.g. of the vagina or of the gastrointestinal tract, thus retains its solidity and integrity. Admittedly, it is beneficial to construct the cladding such that the release mechanism may develop enough force that the cladding ruptures at the moment of release. If it would dissolve before the release, thus before the release mechanism develops enough force, e.g. by swelling or gas-formation, to unfold the preparation, then the fluid surrounding the dosage form, in particular in form of a capsule, might fill up the dosage form and jam the preparation. In particular, for a release mechanism that is mechanically pretensioned, thus can develop the force at any time, such a cladding can be soluble and therefore be the trigger mechanism at the same time.

A trigger mechanism that at least partially seals or covers an aperture respectively a slit may comprise a substance whose solubility depends on a key stimulus, in particular on a pH value of a surrounding medium. For example, a trigger mechanism can at least partially be made out of a substance that is preferably selected from soluble polymer, hydroxypropyl methylcellulose phthalate or Eudragit.

It is to be understood that in particular the predetermined site of action of the release of the sheet like drug may be determined by a pH dependent change of solidity of the trigger mechanism and/or of a substance that is comprised by the trigger mechanism.

It is also within the scope of the present invention that the mobility of one or more elements of the dosage form, in particular a release mechanism, relatively to each other is limited, in particular by a trigger mechanism, in particular in such a way that they remain fixed in their initial position, and that in particular the release mechanism remains fixed in its initial position until the trigger mechanism triggers.

It is to be understood that after the removal of the mobility restrictions, in particular after a property change and/or a conformational change, in particular a change in solidity of the trigger mechanism, the positioning and/or the properties of one or more elements of the dosage form, in particular of the release mechanism, change relatively to each other in such a way that the release mechanism is triggered and the sheet like preparation is released be the release mechanism.

Here, a release by the release mechanism may act upon the release mechanism to release the sheet like preparation by a property change and/or a conformational change, in particular of a change in solidity, of the release mechanism directly and/or a key stimulus, which is equal to or different from the key stimulus triggering the trigger mechanism, directly or by means of intermediate elements, that are selected from the group comprising e.g. pins, levers, springs, cable pulls, and push rods or the like.

In a preferred embodiment of the pharmaceutical dosage form according to the present invention the dosage form, in particular the shell and/or the trigger mechanism, comprises at least one predetermined breaking point.

The term "predetermined breaking point" as used herein is preferably formed as a notch and/or perforation, preferably as notch, that changes its solidity related properties or properties related to something else upon the exposure to a defined pressure.

Such a predetermined breaking point may be a part of the shell, in particular of the capsule of the dosage form, a part of the release mechanism or a part of the trigger mechanism.

In particular, such a predetermined breaking point, preferably a predetermined breaking point formed as a notch in the material, can be made out of the same and/or out of another material out of which the element comprising the predetermined breaking point is made.

For example, a shell made out of hard gelatin can comprise a predetermined breaking point that is also formed out of hard gelatin; in particular, a shell made of hard gelatin can comprise a predetermined breaking point in form of a notch of the hard gelatin.

It is within the scope of the knowledge or the person skilled in the art to determine the properties of a predetermined breaking point in relation to the present invention, in particular its shatter properties by the nature and composition of the material, by the geometric form or by other parameters relating to the solidity.

For example, a predetermined breaking point relating to the present invention can be adapted and/or arranged such that the predetermined breaking point breaks and unblocks the mobility of other elements of the dosage form, in particular of the release mechanism and/or the trigger mechanism, in particular apertures, that control the entry of fluid of the gastrointestinal tract into the dosage form, after an exposure of a predetermined pressure onto the dosage form, in particular onto the predetermined breaking point.

In a preferred embodiment of the pharmaceutical dosage form according to the present invention the shell is formed out of a material that is essentially insoluble in a fluid which is present at the predetermined trigger site and/or predetermined site of action, in particular of the gastrointestinal tract. However, it is to be understood that such a shell may not just be insoluble at the predetermined trigger site but also at other compartments that have to be passed to reach the trigger site and/or the site of action—in other words, on the complete path thereto.

In a preferred embodiment according to the present invention the shell consists of or mainly consists of a material that is essentially insoluble in a fluid which is present at the predetermined trigger site and/or predetermined site of action, in particular of the rectum, of the vagina or of the gastrointestinal tract, preferably vaginal fluid respectively gastric juice.

A material that is essentially insoluble in vaginal fluid respectively gastric juice is preferably selected from the group comprising gastric juice-resistant polymers, comprising acidic polymethacrylates such as methacrylic acid:m-ethyl methacrylate copolymers 1:1 (Eudragit L), methacrylic acid:methyl methacrylate copolymers 1:2 (Eudragit L), methacrylic acid:ethyl acrylate copolymer 1:1 (Eudragit L100-55), acidic cellulose derivatives such as hydroxypropyl methylcellulose acetate succinates (HPMCAS) -LF, -MF and/or -HF and cellulose acetate phthalate; acidic polymers based on vinyl alcohol such as polyvinyl acetate and vinyl acetate: Crotonic acid copolymer; zein, keratin, gluten, shellac, gelatin and alginic acid hardened with formaldehyde or glutaraldehyde.

In this context it is to be understood that a trigger mechanism, in particular when such a trigger mechanism is embodied as a trigger mechanism covering an aperture, is preferably made out of a material that is different to the shell, in particular out of a material that is essentially soluble in the fluid which is present at the predetermined trigger site and/or predetermined site of action, in particular of the rectum, of the vagina or of the gastrointestinal tract, preferably vaginal fluid respectively gastric juice.

In a preferred embodiment of the pharmaceutical dosage form according to the present invention the shell is made out of a material that is selected from the group comprising hard gelatin, polymers, thermoplastics as e.g. Eudragit or the like. In this regard, in particular, materials can be beneficial that have been successfully tested, used and/or authorized already, e.g. for oral dosage forms.

In a further preferred embodiment of the pharmaceutical dosage form according to the present invention the shell consists of a material that is selected from the group consisting of hard gelatin or polymers.

In a preferred embodiment of the pharmaceutical dosage form according to the present invention the shell is formed as a capsule.

In a preferred embodiment of the pharmaceutical dosage form according to the present invention the shell is made of a material which is substantially insoluble in a fluid that is present at a predetermined trigger site or site of action, in particular of the gastrointestinal tract, preferably insoluble in gastric juice, wherein preferably the shell consists of a material which is selected from the group comprising polymers and/or hard gelatin.

Preferably, such an essentially insoluble material, in particular essentially insoluble in vaginal fluid respectively gastric juice, is selected from the group comprising gastric juice-resistant polymers, comprising acidic polymethacrylates such as methacrylic acid:methyl methacrylate copolymers 1:1 (Eudragit L), methacrylic acid:methyl methacrylate copolymers 1:2 (Eudragit L), methacrylic acid:ethyl acrylate copolymer 1:1 (Eudragit L100-55), ammonio methacrylate copolymers (e.g Eudragit RS), acidic cellulose derivatives such as hydroxypropyl methylcellulose acetate succinates (HPMCAS) -LF, -MF and/or -HF and cellulose acetate phthalate; acidic polymers based on vinyl alcohol such as polyvinyl acetate and vinyl acetate: Crotonic acid copolymer; zein, keratin, gluten, shellac, gelatin and alginic acid hardened with formaldehyde or glutaraldehyde. In particular, an ammonio methacrylate copolymer is a material for the shell and/or for the trigger mechanism.

In a preferred embodiment of the pharmaceutical dosage form according to the present invention the dosage form, in particular the shell and/or the trigger mechanism, comprises a wick system, in particular a capillary system, that is adapted to direct fluid into the dosage form by capillary forces.

Such a wick system advantageously allows a, preferably predetermined and/or controlled, entry of a fluid out of a tissue, in particular by capillary forces, into the dosage form, in particular into an inner space of the shell, by the capillary action of the wick system.

In a preferred embodiment of the pharmaceutical dosage form according to the present invention the dosage form, in particular the shell and/or the trigger mechanism, comprises a wick system.

In a preferred embodiment of the pharmaceutical dosage form according to the present invention the release mechanism or a part thereof is an expansion mechanism or comprises such an expansion mechanism.

The term "expansion mechanism" as used herein preferably refers to a release mechanism for releasing the sheet like preparation that is adapted such that the sheet like preparation is expandable to a predetermined extent by the release mechanism, i.e. upon activation of the release mechanism the sheet like preparation is expanded to this predetermined extent or extends to it, respectively. For example, the sheet like preparation, in particular a wafer, can be contained in the shell with a smaller spatial extent, e.g. lumped together, collapsed or folded or brought into a smaller format in another way. A release mechanism comprising an expansion mechanism or an expansion mechanism that is realized as a release mechanism or as a part thereof is preferably adapted to stretch respectively expand the sheet like preparation, which is contained in the shell with a smaller spatial extent, to a predetermined size upon activation of the release mechanism, in particular to spread out, to open or to unfold the sheet like preparation or to bring it to a larger size in some other way.

This advantageously makes it possible to provide a relatively small dosage form, in particular for rectal, oral or vaginal application, wherein the surface area of the sheet like preparation may be particularly advantageously increased by an expansion or the sheet like preparation, in particular for the active ingredient release at the predetermined site of action. Additionally, also the surface of a predetermined site of action, in particular of the vagina, of the rectum or of the gastrointestinal tract, e.g. a mucous membrane or an intestinal wall, which is in contact with the sheet like preparation, may be increased.

In a preferred embodiment of the pharmaceutical dosage form according to the present invention the expansion mechanism is selected from the group comprising mechanical expansion system, gas driven expansion system, compressed foam or compressed tissue.

In a variation of the present invention the expansion mechanism is a gas driven expansion system. Such a gas driven expansion system may comprise a pressure vessel which can be filled with a gas-forming agent.

Advantageously, a gas formed by a gas-forming agent may affect the expansion of the sheet like preparation.

In a preferred embodiment of the pharmaceutical dosage form according to the present invention the release mechanism, in particular the expansion mechanism, comprises a gas-forming agent, that is preferably selected from the group comprising sodium hydrogen carbonate and citric acid.

In a variant of the present invention the expansion system is a mechanical expansion system. Such a mechanical expansion system may be constructed as a joint or lever expander. In particular, such a mechanical expansion system can be constructed such that the shell comprises at least one joint or lever element that is preferably arranged at a free end of the shell.

In a preferred embodiment of the pharmaceutical dosage form according to the present invention the expansion mechanism is adapted in such a way that an expansion of the expansion mechanism results in an at least partially opening of the shell.

The at least partially opening of the shell advantageously allows the release of the sheet like preparation at a predetermined site of action, in particular of the vagina, of the rectum or of the gastrointestinal tract.

In a preferred embodiment of the pharmaceutical dosage form according to the present invention the dosage form contains the preparation in a folded form and the expansion mechanism is adapted such that the expansion of the expansion mechanism results in an unfolding of the preparation.

Preferably, an unfolding of the preparation may also cause the opening of the shell, in particular capsule.

This advantageously allows to provide a relatively small dosage form, wherein in a particularly advantageous manner the surface area of the sheet like preparation like preparation may be increased by an unfolding of the sheet like preparation, in particular to release the active pharmaceutical ingredient at a predetermined site of action, e.g. at a mucous membrane.

In a preferred embodiment of the pharmaceutical dosage form according to the present invention the shell, preferably the wick system, if present, contains a gas-forming agent as release mechanism, in particular as expansion mechanism, wherein the gas-forming agent is selected from the group comprising sodium hydrogen carbonate, citric acid, sodium dihydrogen phosphate, pressurized gas, liquefied gas, and boiling liquid.

It is to be understood that preferably after an unblocking of an aperture by a trigger mechanism a wick system directs a fluid surrounding the dosage form at a predetermined site of action, in particular of the rectum, of the vagina or of the gastrointestinal tract, to a gas-forming agent, that thereupon forms a gas, e.g. carbon dioxide by a chemical reaction, which expands respectively inflates a gas tight shell that can be filled with a gas, in particular a balloon.

In a preferred embodiment of the pharmaceutical dosage form according to the present invention the preparation is formed as a gas tight shell, in particular as a balloon, that can be filled with gas, and/or the dosage form contains the preparation in a folded form, preferably as a gas tight shell that can be filled with a gas, in particular as a balloon.

It is to be understood that such a preparation formed as a gas tight shell that can be filled with gas, can be expanded, preferably by an expansion mechanism, in particular by a gas driven expansion system, and can be released at a predetermined site of action, in particular of the gastrointestinal tract. In a particularly advantageous manner the gas tight shell, in particular balloon, that can be filled with a gas can be expanded, in particular inflated, by introducing a gas into the gas fillable shell, in particular balloon. The thereby resulting pressure within the shell that can be filled with a gas, in particular balloon, preferably causes a close contact of the outer surface area of the gas fillable shell at the predetermined site of action, in particular of a mucous membrane or intestinal wall. Additionally advantageously, the mucous membrane or intestinal wall respectively a section of the mucous membrane or intestinal wall may be slightly stretched such that an advantageously increased surface area for the resorption of the active pharmaceutical ingredient is available.

In an alternative preferred embodiment of the pharmaceutical dosage form according to the present invention, the gas tight shell can be filled with a gas, in particular balloon, comprises and/or the dosage form, in particular the shell comprises a gas tight, gas fillable shell in a folded form, wherein the gas fillable shell, in particular balloon, is coated with the sheet like preparation.

In a preferred embodiment of the pharmaceutical dosage form according to the present invention the gas-forming agent is arranged in a part of the shell that preferably is opposed to the part of the shell containing the preparation and/or that is preferably facing the part of the shell containing the preparation.

Furthermore, the shell may be at least partially slit at such a part of the shell that is opposed to the part of the shell containing the preparation and/or that is facing the part of the shell containing the preparation, such that preferably the shell may be pushed open by the gas fillable shell, in particular balloon, upon expansion by filling with a gas, such that the shell that can be filled with a gas, in particular balloon, may enter e.g. into the lumen of the rectum, of the vagina or of the gastrointestinal tract.

It is to be understood that in such an arrangement the shell may be pushed open at such a slit, preferably by the pressure developed by means of the introduced gas, and the shell that can be filled with a gas, in particular the balloon, may be released.

In an preferred embodiment of the pharmaceutical dosage form according to the present invention the dosage form contains the preparation, preferably as a gas tight shell that can be filled with a gas, in particular as a balloon, and the gas tight shell that can be filled with a gas comprises an aperture that is circumferentially attached at an inner border of the shell.

Preferably, the border of such an aperture is attached at the inner border of the shell, such that gas out of the inner space of the shell can stream into the gas tight shell that can be filled with a gas, in particular into a balloon.

In a preferred embodiment of the pharmaceutical dosage form according to the present invention the shell is divided at its periphery.

In a preferred embodiment of the pharmaceutical dosage form according to the present invention the shell, in particular the expansion mechanism, preferably mechanical expansion system, comprises at least a first joint or lever element, preferably a hinge. Such a joint or lever element, in particular a first joint or lever element, is advantageously arranged in such a way that a shell, preferably a shell divided at its periphery, in particular when it comprises several parts that a pivotally connected with such a joint of lever element may swing open or open up. Such a joint or lever element, in particular a first joint or lever element, can be advantageously embodied, in particular, as a mechanical hinge, as a paper and/or by means of an incorporated material with elastic properties. In particular, this joint or lever element can be formed as an integer part of the shell or can be connected (e.g. glued) to it.

The sheet like dosage form, in particular a wafer, may be contained in an inner space of the shell in a folded form and may be attached to a side, in particular to one or more edges of the, preferably multi-part, shell, that is opposed to the first joint or lever element, in particular hinge, in such a way that turning or opening respectively swinging out or swinging open the shell or a part of the shell by means of the first joint or lever element expands, in particular unfolds, and/or opens up the sheet like dosage form.

In order to assist such an expansion, in particular an unfolding, of the sheet like preparation like dosage form, the dosage form may contain further elements.

In particular, such further elements can be arranged in such a way that a flip angle is advantageously enlarged such that the release of the sheet like preparation is enhanced. For this purpose, the shell may comprise one or more further joint or lever elements or flexible parts additionally to the first joint or lever element. In this context, it is to be understood that joint or lever elements may be adapted in such a way that they can open up the preparation. Additionally or alternatively, further elements may be embodied that perform only this task. Also sections of a multi-part shell may perform this task. In other words, e.g. rods and bows may be provided that open up the preparation and/or the dosage form, in particular to obtain a "tent like" structure. Additionally or alternatively, also sponges or something similar may be used in an advantageous manner, wherein they can open up the dosage form, however in particular, they cannot contribute to the movement of the expansion or can contribute to it only to a small amount. Moreover, lever systems can be provided that realize a kind of a transmission stage that turn a small movement of the release mechanism into a big movement of the whole dosage form.

In an embodiment with a shell that is divided at its periphery and/or comprises a slit, the unwanted entry of fluid surrounding the shell and/or the dosage form into the shell, in particular into an intermediate space between two edges of the shell, may be advantageously avoided, when a slit and/or a slit occurring at the edges of two parts of a shell that is divided at its periphery, is at least partially covered by a sealing. In particular, a sealing can be made out of a flexible material that is e.g. waxen or gummy. In particular, it is beneficial if possible unevenness at the edges of the shell is compensated in this way. Alternatively or additionally, the slit and/or a slit, that is present at the edges of two parts of the shell which is divided at its periphery, may also be sealed against unwanted entry of fluid into the shell, wherein the fluid surrounds the shell and/or the dosage form. Further, alternatively or additionally, the slit and/or a slit occurring at the edges of two parts of the shell that is divided at its periphery may be completely or partially coated with a sealing, in particular at an inner wall and/or outer wall of the shell, and/or may be coated, at least partially with a trigger mechanism.

In this context, it is also within the scope of the present invention that a slit and/or a slit occurring at the edges of two parts of the shell that is divided at its periphery may be an aperture of the shell and/or of the trigger mechanism according to the different embodiments of the present invention.

It is also within the scope of the present invention that a sealing and/or a trigger mechanism may be adapted in such a way that it ruptures upon the opening of the shell, in particular upon a flipping open of the shell, or that it dissolves beforehand.

In a preferred embodiment of the pharmaceutical dosage form according to the present invention the shell, in particular the expansion mechanism, preferably mechanical expansion system, comprises at least one spring element.

For example, such a spring element can be arranged in such a manner that the spring element effectuates the opening of the shell, in particular a flipping open of the shell. For this purpose, the spring element may be constructed as a pretensioned spring element, in particular a pretensioned spring, that applies a spring force to the shell or to a part thereof, wherein the spring force is sufficient to flip open the shell. A sealing and/or a trigger mechanism may counteract this flipping open or opening of the shell effectuated by the spring. After dissolving and/or rupture of the sealing and/or of the trigger mechanism, the opening, in particular flipping open, of the shell effectuated by the spring can take place. Additionally or alternatively, also further elements may be present, that transfer the movement of the spring, e.g. this function can also be achieved, as described herein, by a hinge, a lever or a joint element.

In a preferred embodiment of the pharmaceutical dosage form according to the present invention the preparation comprises a swelling agent, wherein the swelling agent preferably is selected from the group comprising sponge and fibers.

Preferably, the swelling agent is arranged in the shell or in a part thereof. After a triggering of the trigger mechanism the swelling agent may be arranged in such a manner that the preparation is released, in particular unfolded, at a predetermined site of action, in particular of the gastrointestinal tract, and/or that the preparation is applied to the predetermined site of action, e.g. a mucous membrane or an intestinal wall. For this purpose, it is preferred that the swelling agent forms a part or is a release mechanism, in particular expansion mechanism. Preferably, the swelling agent is a sponge or comprises fibers, in particular compressed layers of fibers that preferably comprise cellulose and/or consist of another suitable swellable material.

In a preferred embodiment of the pharmaceutical dosage form according to the present invention, the shell comprises at least a first tube element and, optionally, at least one further tube element.

In a preferred embodiment of the pharmaceutical dosage form according to the present invention, the shell comprises a first tube element and at least a second tube element, wherein the second tube element has a smaller tube diameter than the first tube element.

Preferably, the shell is formed by at least one first and/or at least one first and at least one further tube element.

In a preferred embodiment of the pharmaceutical dosage form according to the present invention a shell comprises a first tube element and at least a second tube element, wherein the second tube element has smaller tube diameter than the first tube element, and wherein the second tube element is at least partially arranged respectively inserted into the first tube element.

In a preferred embodiment of the pharmaceutical dosage form according to the present invention the shell comprises at least a first tube element, at least a second tube element, and a spring element, preferably a compression spring, wherein the spring element is arranged such that the spring element can move the at least one second tube element longitudinally relative to the first tube element.

It is to be understood that such a spring element, preferably within the shell, in particular in an inner space of the shell, preferably at least within a tube element, is arranged in such a manner that this spring element applies a spring force to the shell, in particular to the at least one first and/or to the at least one further spring element, that is sufficient to move the second tube element longitudinally relative to the first tube element. A sealing and/or a trigger mechanism may counteract this unfolding or opening of the shell effectuated by the spring. After dissolving and/or rupture of the ceiling and/or the trigger mechanism the spring driven displacement of the tube elements can take place. Such a displacement of tube elements may result in an opening of the shell and/or release of the sheet like preparation. In particular, the drug can be applied onto the smaller tube and is then pushed out of the shell, whereafter even more one or more further tubes with preparations may be released. Alternatively, further appropriate steps can be provided after moving out the tube that release the preparation. In particular, the displacement may serve as a preparation of the release. In this context, it is also to be understood that the specific configuration is selected depending on the desired final size of the dosage form and/or of the preparation.

Furthermore, the shell and/or a first and/or a further tube element may comprise a mechanical stop that limits the displacement of the least one second tube element in the longitudinal direction relative to the first tube element.

In a preferred embodiment of the pharmaceutical dosage form according to the present invention the shell comprises at least one joint or lever element, that is preferably arranged at a free end of the shell.

In a preferred embodiment of the pharmaceutical dosage form according to the present invention the first joint or lever element is arranged at a free end of the shell.

In particular, a first joint or lever element may be arranged at a free end of the shell, preferably at the free end of a first and/or of a further tube element, that comprises a rotatably mounted lever.

In a preferred embodiment of the pharmaceutical dosage form according to the present invention the shell comprises at least a further joint or lever element.

In a preferred embodiment of the pharmaceutical dosage form according to the present invention the first joint or lever element and/or the further joint or lever element is formed as a joint, hinge and/or lever or comprises a joint, hinge and/or lever.

Preferably, a first joint or lever element and/or at least a further joint or lever element can be aligned in such a way that they can carry out their joint or lever movement in different, preferably opposing, directions. A joint angle of a first joint or lever element and/or of a at least one further joint or lever element, in particular with regard to the shell, or a part thereof, in particular a tube element, may be chosen in such a manner and/or be adjustable, in particular swiveling, that an expansion of the sheet like preparation is achieved and/or is made possible by a movement of the joint or lever. In particular, the diameter of the preparation can be enlargeable by a joint or lever movement.

It is also within the scope of the present invention that a joint or lever element, in particular a lever, may directly be hinged by a spring element or by intermediate elements.

In a preferred embodiment of the pharmaceutical dosage form according to the present invention the first joint or lever element and/or the further joint or lever element is at least partially covered by the trigger mechanism.

For example, in an initial state of the dosage form a joint or lever element or a plurality of joint or lever elements, in particular levers, can form the shell of the dosage form or at least a part thereof. An unwanted entry of fluid at the edges of the joint or lever element respectively of the joint or lever elements into the dosage form may be avoided by sealings, form fit or coatings of the inner and/or outer wall of the joint or lever elements. Such sealings or coatings may rupture upon opening of the shell, in particular upon an expansion of the expansion system, and/or upon a joint or lever movement of the joint or lever elements or may dissolve before that.

In a preferred embodiment of the pharmaceutical dosage form according to the present invention the at least one first joint or lever element and/or the at least one further joint or lever element is arranged in such a way that a respective joint or lever element, in particular a lever, of one end is arranged adjacent to a joint or lever element, in particular lever, of the other end. Preferably, the at least one first joint or lever element and/or the at least one further joint or lever element is pivotally and/or rotatably mounted at a first or further tube element. Preferably, the tube elements can comprise a slit in which at least a part of the at least one first joint or lever element and/or of the at least one further joint or lever element can perform a sliding movement—preferably driven by a spring—in particular in the direction of the end of the tube.

Preferably, the joint or lever elements of a first tube and the joint or lever elements of a second tube are arranged alternately in a closed state of the dosage form such that preferably, in a closed state the joint or lever elements of the first tube and the joint or lever elements of the second tube form a cladding or a shell.

In particular, in an arrangement, in which the joint or lever elements of a first tube and the joint or lever elements of a second tube are arranged alternately in a closed state of the dosage form, the lever length between the joint or lever elements of a first tube and the joint or lever elements of a second tube may extend over the whole length of the folded dosage form. It is to be understood that the maximum lever length might be limited to half the length of the dosage form in a case, in which the lever or joint elements are arranged opposing each other, and that, in particular, the maximally achievable extension might be smaller.

Alternatively, the joint or lever elements of a first tube and the joint or lever elements of a second tube may also, at least partially, be superimposed and/or overlap in a closed state, wherein the joint or lever elements are arranged such that the joint or lever elements do not obstruct each other upon a release according to the invention.

The arrangement of a first and/or of a second tube element and the arrangement of lever and joint elements can be chosen such, in particular, that the lever and/or joint elements form a wreath structure, which can be attached at the tube element that is facing the viewer, when viewing the dosage form from the rear, thus looking at the smallest area of the dosage form. In such an arrangement it would be beneficial if the joint or lever elements of a first tube and the joint or lever elements of a second tube are arranged alternately, preferably in a closed state of the dosage form, so that, preferably in a closed state in which the joint or lever elements of the first tube and the joint or lever elements of the second tube form a shell and/or a cladding, the wreath structure at a first end of the dosage form, in particular at an end of the first tube element, and the wreath structure at a second end of the dosage form, in particular at an end of a second tube element, are offset in a rotationally symmetric manner. In this context it is to be understood that preferably a joint or lever movement of the first joint or lever element and/or of the at least one further joint or lever element causes an unfolding of a sheet like preparation that is in a folded form within the dosage form in an initial state, such that the sheet like preparation unfolds at a predetermined site of action in a particularly advantageous manner, and preferably may contact a mucous membrane or the intestinal wall.

A lever respectively lever element, as used herein, preferably refers to a mechanical force transformer, preferably comprising a rigid body that is rotatably attached at a pivotal point. A hinge, as used herein, preferably refers to a movable connection of two planes, in particular of two parts of a shell, preferably of an edge. In particular, a hinge, preferably a connecting joint of one or more joint or lever elements, is arranged in such a manner that two parts of the shell are moveably connected, for example in order to obturate an inner space of the shell by a moveable construction element, in particular by parts of the shell. For the purpose a hinge is constructed in such a way that it can bear the load of the moveable part and the force of the movement. A hinge, as used herein, may be constructed as a bearing with one degree of freedom.

Within the scope of the present invention a joint element, in particular lever, may be adapted such that a contact of the sheet like preparation with a predetermined site of action, in particular with a mucous membrane or intestinal wall is strengthened by connecting of joint or lever elements opposing each other, in particular levers, preferably comprising at least one further flexible element.

It is to be understood that preferably a movement of a mechanical expansion system and/or joint or lever element, preferably embodied as a part of a release mechanism, is triggered by a trigger mechanism. Such a trigger mechanism may, for example, comprise a soluble polymer that locks the mechanical expansion system and/or joint or lever element(s), in particular levers, in its respectively their initial positions to each other. At an intended contacting with a fluid at a predetermined site of action, in particular with a fluid of the gastrointestinal tract, the polymer may loosen and a spring element, if present, may trigger and/or effectuate the movement of the mechanical expansion system and/or of the joint or lever element, in particular of the lever. Additionally or alternatively, a mechanical expansion system and/or joint or lever element(s), in particular levers, may be pretensioned in an initial state and/or may at least partially form a spring element such that the energy stored in a mechanical expansion system and/or joint or lever element, in particular lever in this manner is released by triggering of the trigger mechanism and the mechanical expansion system and/or joint or lever element, in particular lever, moves as intended. For example, after triggering of the trigger mechanism the sheet like preparation can be released by pushing apart of tube elements that are at least partially engaged in a telescopic manner, for example by a spring element, by stretching and/or unfolding a sheet like preparation that is contained in the shell in a folded form by the expansion mechanism and/or joint or lever elements.

In a preferred embodiment of the pharmaceutical dosage form according to the present invention the sheet like preparation is a wafer.

In particular, the sheet like preparation of a dosage form according to the invention can be formed as a so-called wafer. Such a wafer can fit to the irregular surface contour of a predetermined site of action, in particular of a mucous membrane, for example of the intestinal, rectal or vaginal wall, after absorption of moisture. Additionally, a sheet like preparation of a dosage form according to the invention may be gellable or swellable.

In a preferred embodiment the sheet like preparation of a dosage form according to the invention is already flexible and stretchable before it is released out of the shell and can absorb a fluid entering the shell, e.g. from the gastrointestinal tract.

In a preferred embodiment of the pharmaceutical dosage form according to the present invention the thickness of the sheet like preparation is 0.01 mm to 2 mm, preferably 0.03 mm to 1 mm, preferably 0.05 mm to 0.1 mm.

In particular, this is beneficial to provide a sheet like preparation with a relatively small thickness.

In a preferred embodiment of the pharmaceutical dosage form according to the present invention the sheet like preparation has an area between 0.5 and 25 $cm^2$, preferably between 1 to 10 $cm^2$.

The sheet like preparation may have different shapes. In particular, a sheet like preparation can have a round, triangular, quadrangular or polygonal shape.

In a preferred embodiment of the pharmaceutical dosage form according to the present invention the sheet like, in particular film shaped, foil shaped or wafer shaped, preparation, that comprises the active pharmaceutical ingredient, contains an active pharmaceutical ingredient with a drug content of 0.5 to 40% by weight, preferably 1 to 30% by weight, and most preferred 5 to 20% by weight.

In a preferred embodiment of the pharmaceutical dosage form according to the present invention the sheet like, in particular film shaped, foil shaped or wafer shaped, preparation comprising the active pharmaceutical ingredient has a single-layered or multi-layered structure out of a single or multiple layers, wherein at least one (preferably first) layer contains an active pharmaceutical ingredient.

It is to be understood, that such a first layer containing the active pharmaceutical ingredient may be any layer of a multi-layered preparation with regard to its arrangement and that it is, in particular, not limited to an outer, inner, bottom or upper layer.

In a preferred embodiment of the pharmaceutical dosage form according to the present invention the sheet like, in particular film shaped, foil shaped or wafer shaped, preparation, that comprises the active pharmaceutical ingredient, comprises a multi-layered structure of multiple layers, wherein at least a first layer contains a first active pharmaceutical ingredient and wherein at least a further layer contains at least a further active pharmaceutical ingredient.

It is also within the scope of the present invention that the active pharmaceutical ingredient contained in a first layer is equal to or different from an active pharmaceutical ingredient contained in a further layer. In particular, a sheet like preparation of a dosage form according to the invention can be embodied as a so-called combination wafer and can contain a combination of active pharmaceutical ingredients of at least two active pharmaceutical ingredients in one or more layers individually or jointly.

In a preferred embodiment of the pharmaceutical dosage form according to the present invention the sheet like, in particular film shaped, foil shaped or wafer shaped, preparation comprising the active pharmaceutical ingredient comprises at least a first layer containing the active substance and/or a further layer containing the active substance, wherein the first layer containing the active substance and/or the further layer containing the active substance comprises a polymer, preferably a film forming polymer.

Such a layer comprising a polymer, preferably a film forming polymer advantageously serves as an active ingredient reservoir, wherein such a layer can release the active pharmaceutical ingredient under the effect of a fluid.

In a preferred embodiment of the pharmaceutical dosage form according to the present invention the sheet like, in particular film shaped, foil shaped or wafer shaped, preparation comprising the active pharmaceutical ingredient comprises at least one first layer containing the active ingredient and/or a further layer containing the active ingredient, wherein the at least one first layer containing the active ingredient, and/or the further layer containing the active ingredient comprises a polymer, and wherein the polymer fraction in the at least one first layer containing the active substance and/or the further layer containing the active substance, which contains the polymer, is at least 10 to 90% by weight, preferably 20 to 70% by weight, and more preferred 30 to 60% by weight.

In a preferred embodiment of the pharmaceutical dosage form according to the present invention the sheet like, in particular film shaped, foil shaped or wafer shaped, preparation comprising the active pharmaceutical ingredient comprises at least a first layer containing the active ingredient and/or a further layer containing the active ingredient, wherein the at least one first layer containing the active ingredient and/or the further layer containing the active ingredient is an adhesive layer.

In a preferred embodiment of the pharmaceutical dosage form according to the present invention the at least one first layer containing the active ingredient and/or the further layer containing the active ingredient comprises a polymer, preferably a film forming polymer, wherein the polymer is a film forming polymer that is water dispersible and/or decomposable and/or water disintegrable.

A polymer for a first layer containing an active substance and/or for a further layer containing an active substance may, in particular, be selected from a group comprising polyvinyl alcohols, Polyvinylpyrrolidone, polyvinyl acetate, polyethylene glycol, polyethylene oxide polymers, polyurethanes, polyacrylic acids, polyacrylates, polymethacrylates, poly (methyl vinyl ether-maleic acid anhydrides), starch, starch derivates, natural gums, alginates, pectins and gelatin, Pullulan, gel forming proteins, Chitosan, Agar-Agar, agarose, carrageenan, xanthan, tragacanth, dextran, and cellulose ethers such as ethyl cellulose, hydroxyethyl cellulose, propyl cellulose, carboxymethyl cellulose, sodium-carboxy methylcellulose, hydroxypropyl cellulose, hydroxypropyl methylcellulose, hydroxypropyl ethyl cellulose, cellulose acetate, povidone and copovidone.

The polymers may be used individually or in a combination with each other in order to manufacture a sheet like preparation for the dosage form according to the invention with the desired properties as adhesion, release or disintegration properties. In particular, a sheet like preparation according to the invention can consist of a single polymer layer. Also, a sheet like preparation for a dosage form according to the invention may have a structure with two or multiple layers, when at least one of the layers contains an active pharmaceutical ingredient. If multiple layers contain the active pharmaceutical ingredient or the active pharmaceutical ingredients, they may differ from each other in their active ingredient content and in their combination of active ingredients, but also in their polymer composition and thus their adhesion and/or decomposition properties.

In a preferred embodiment of the pharmaceutical dosage form according to the present invention the sheet like, in particular film shaped, foil shaped or wafer shaped, preparation comprising the active pharmaceutical ingredient comprises at least one first active ingredient free layer, that does not contain an active pharmaceutical ingredient.

In a preferred embodiment of the pharmaceutical dosage form according to the present invention the sheet like, in particular film shaped, foil shaped or wafer shaped, preparation comprising the active pharmaceutical ingredient comprises at least a further active ingredient free layer that does not contain an active pharmaceutical ingredient.

In a preferred embodiment of the pharmaceutical dosage form according to the present invention the first active ingredient free layer and/or the at least one further active ingredient free layer is a water insoluble layer which preferably comprises water insoluble substances selected from the group ethyl cellulose and/or combinations of ethyl cellulose with other water insoluble substances, hydrophobic plasticizers, especially triethyl citrate, and/or dies and/or fragrances and/or flavorings.

In particular, the use of ethyl cellulose may be beneficial due to its properties comprising a good processability, biocompatibility, and water insolubility.

In a preferred embodiment of the pharmaceutical dosage form according to the present invention the first active ingredient free layer and/or the at least one further active ingredient free layer is an adhesive layer that preferably comprises hydroxypropyl methylcellulose.

The adhesive layer may vary in its desired thickness. Additionally or alternatively, the adhesive layer may be a mucoadhesive polymer selected from the group comprising cellulose derivates, starch and starch derivates, polyvinyl alcohol, polyethylene oxide, polyethylene, polypropylene, polyacrylic acid and polyacrylate derivates, Polyvinylpyrrolidone, Povidone, Copovidone, Sodium alginate, gelatin, Xanthan gum, Carrageenan, pectins, dextrans, lectins, Chitosan, Pullulan, and mixtures thereof.

The adhesive layer may vary in its desired thickness. Additionally or alternatively, the adhesive layer may comprise a solvent that is selected from the group comprising water, Ethanol, Methanol, Acetone, organic solvents, and mixtures thereof.

Furthermore, the adhesive layer may additionally contain additives such as colorants, fragrances, flavoring agents, preservatives, antioxidants, penetration enhancers, solubilizers, disintegration accelerators, pore formers, lubricants, and mixtures thereof.

In a preferred embodiment of the pharmaceutical dosage form according to the present invention the sheet like preparation has a multi-layered structure, preferably with two or three layers, and comprises at least one layer containing an active substance and at least one active ingredient free layer.

In a preferred embodiment of the pharmaceutical dosage form according to the present invention the sheet like preparation comprises a multi-layered structure, preferably with three layers, wherein a first layer containing an active ingredient and/or a further layer containing an active ingredient is arranged between a first active ingredient free layer and/or a further active ingredient free layer, wherein, preferably, the first active ingredient free layer is a water insoluble layer, that preferably comprises ethyl cellulose, and the at least one further active ingredient free layer is an adhesive layer, that preferably comprises hydroxypropyl methylcellulose.

A drug according to the present invention, in particular a sheet like preparation, may additionally contain one or more additives. In particular, the following substances are eligible as additives: lubricants, lubricants, glidants, binders, additional active ingredients, disintegrants, antioxidants, chelating agents, coating agents, flow agents, preservatives, fillers, surfactants, plasticizers, and pigments. Furthermore, the additives may be selected from the following group: pore formers, penetration enhancers, solubilizers, emulsifiers, comprising polyethoxylated sorbitan fatty acid esters, ethoxylated fatty alcohols, and lecithin; plasticizers, comprising polyethylene glycol, glycerol and other polyhydric alcohols, higher alcohols such as dodecanol, undecanol, or octanol, sorbitol, mannitol and other sugar alcohols, dexpanthenol and triglycerides; fillers comprising highly disperse silicon dioxide, titanium dioxide, zinc oxide, chalk and starch; colorants; sweetening and flavoring agents; wetting agents; preservatives; pH regulators and antioxidants; disintegration accelerators; permeation enhancers which improve the resorption of estradiol into the mucous membrane, for example, fatty acids and fatty acid esters, polyhydric alcohols such as propanediol, tocopherols or essential oils such as menthol. The fraction of these additives may be up to 60% by weight relative to the total weight of the sheet like preparation. Preferably, the fraction of the additives is between 5 and 40% by weight. By adding one or more of said additives, the person skilled in the art can specifically influence the chemical and physical properties of the film shaped drug containing the active ingredient such that, for example, a desired flexibility, adhesivity, swellability or decomposability as well as diffusion properties may be adjusted.

According to a preferred embodiment the pharmaceutical dosage form, in particular the sheet like preparation, according to the invention is intended to enable a time delayed active ingredient release. The active pharmaceutical ingredient is preferably released over a period of 4 hours, preferably over a period of 6 hours and most preferably over a period of 8 hours. In order to achieve a delayed active ingredient release in case of two-layered or multi-layered preparations, at least one of the layers containing an active ingredient, in particular a polymer layer, has a delayed active ingredient release.

For a delayed active ingredient release the film shaped medicaments are preferably formulated as slowly soluble or slowly disintegrating film which are completely disintegrated or dissolved only after several hours. Preferably, they are completely disintegrated or completely dissolved only after 4 hours, preferably only after 6 hours, and even most preferably only after 8 hours or even only after more than 24 hours.

According to an alternative preferred embodiment the pharmaceutical dosage form according to the invention, in particular the sheet like preparation is a rapidly releasing dosage form which releases the active pharmaceutical ingredient within 1 hour, preferably within 30 minutes, and even most preferably within 5 minutes. For a rapid active ingredient release the film shaped preparation may preferably be formulated as a fast dissolving or rapidly disintegrating film. The sheet like preparation is adapted to essentially completely disintegrate, to transition to a gelatinous state or to dissolve preferably within a few minutes after the release. Preferably, the sheet like preparation is completely disintegrated, transitioned into a gel state or completely dissolved within 1 hour, preferably within 30 minutes, more preferably within 15 minutes, and particularly most preferably within 5 minutes.

According to a preferred embodiment the film shaped medicaments according to the invention are adhesive, in particular mucoadhesive. An embodiment that comprises only an adhesive, in particular mucoadhesive surface, is particularly preferred. Thereby, a sticking of the drug formulation to a predetermined site of action, in particular a mucous membrane, during the application duration is achieved and the active pharmaceutical ingredient or the active pharmaceutical ingredients can be resorbed directly at a predetermined site of action, in particular through a mucous membrane.

Furthermore, a sheet like preparation may comprise a layer at a side that is opposed to the adhesive, in particular mucoadhesive surface, wherein said layer is impermeable for the active pharmaceutical ingredient such that at the application at a predetermined site of action a directed active ingredient release can be achieved.

The pharmaceutical dosage form, in particular the sheet like preparation, can be prepared by a person skilled in the art by basically known methods, for example by coating of an inert support with a liquid composition which comprises the polymer(s), active pharmaceutical ingredient(s) and optionally additive(s) and solvent(s), by means of e.g. a method involving a doctor blade, spray processors or extrusion processors. The thin film layer obtained in such a way is dried. For a multi-layered sheet like preparation one or more coatings may be applied onto the existing film layer in the same manner or may be manufactured separately and then be subsequently laminated.

A pharmaceutical dosage form, in particular the shell and/or the sheet-like preparation, may further comprise at least one taste-masking additive. This advantageously allows the masking of a bitter or in some other way unpleasant tasting active pharmaceutical ingredient but may also be beneficial to accelerate the onset of effect of an active pharmaceutical ingredient. Taste-masking additives are known to the person skilled in the art. Such a taste-masking additive may, in particular, comprise a sugar alcohol selected from mannitol, sorbitol, xylitol, malitol, lactitol, erythritol, threitol, and isomalt as well as sodium hydrogen carbonate.

An active pharmaceutical ingredient contained in a sheet-like preparation of the pharmaceutical dosage form according to the invention may, in particular, be selected from the group comprising proteins and peptides, in particular insulin, buserelin, oesmospressin, calcintonin and estrogen as well as biotechnologically manufactured drugs such as the antibody rituximab. Here, it is to be understood that proteins and peptides, in particular insulin, buserelin, oesmopressin, calciotonin and estrogen may display, under certain circumstances, a bad—in particular a bad oral—bioavailability and thus are good candidates for the application by means of the dosage form according to the present invention.

Substances from the following groups are particularly suited as active pharmaceutical ingredients: drugs acting on the skeleton and the muscles, drugs acting on the nervous system, hormones and drugs acting on the hormonal system, gynecologic acting drugs, drugs acting on the cardio-vascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides.

In particular, the sheet like preparation may comprise at least a first region and at least a second region, wherein the at least one first region comprises the active pharmaceutical ingredient. Preferably, the at least one second region comprises a further active pharmaceutical ingredient that is different from the active pharmaceutical ingredient of the at least one first region of the sheet like preparation. Also preferably, the at least one second region does not comprise the active pharmaceutical ingredient of the at least one first region of the sheet like preparation. Alternatively and preferably, the at least one second region comprises the active pharmaceutical ingredient of the at least one first region of the sheet like preparation with a concentration by area, volume or mass that is different from the concentration of the active pharmaceutical ingredient of the first region.

It is to be understood, that in this context active pharmaceutical ingredients may also refer to mixtures of active pharmaceutical ingredients and/or additives. Thus, the at least one second region of the sheet like preparation may comprise a mixture that differs from the mixture of the at least one first region. In particular, the mixtures of the at least one first region and of the at least one second region may differ in the composition of active pharmaceutical ingredients and/or additives as well as in the amount of the respective active pharmaceutical ingredients and/or additives.

In particular, this advantageously allows releasing different active pharmaceutical ingredients to different regions of the body, in particular to different mucous membranes or to different regions of a mucous membrane such as buccal, oral, esophageal, gastric, intestinal, rectal or vaginal mucosa, with a single pharmaceutical dosage form. Preferably, one active pharmaceutical ingredient or one mixture of active pharmaceutical ingredients can be applied to a first region of the vaginal mucosa that is closer to the cervix than a second region of the vaginal mucosa and another active pharmaceutical ingredient or another mixture can be applied to said second region. Moreover, no active pharmaceutical ingredients may be released to the first or the second region of the vaginal mucosa. Alternatively and preferably, the first region of the sheet like preparation may be in contact with an esophageal mucosa and the second region of the sheet like preparation may be contact with a buccal mucosa. In this way, the esophageal mucosa can be treated with the active pharmaceutical ingredient while the buccal mucosa is treated with another active pharmaceutical ingredient, not treated or an additive is released to the buccal mucosa. In particular, a flavoring agent and/or a local anesthetic may be released, particularly to increase or decrease the production of saliva and/or to make the application of the pharmaceutical dosage form more pleasant and/or to suppress the urge to gag.

In a preferred embodiment of the pharmaceutical dosage form according to the present invention, in which the sheet like preparation comprises at least a first region and at least a second region, the second region may comprise a further active pharmaceutical ingredient that counteracts the active pharmaceutical ingredient of the first region. This may be beneficial to suppress a systemic effect of the active pharmaceutical ingredient of the first region. In particular, a fluid that passes along the mucous membrane may pass, at first, the first region and then the second region, and therefore may, at first, take up the active pharmaceutical ingredient of the first region, which is then counteracted, preferably neutralized, by the further active pharmaceutical ingredient of the second region. In particular, such an active pharmaceutical ingredient counteracting the other pharmaceutical ingredient can be chosen from the following list: enzymes that break down active pharmaceutical ingredients such as esterases; ions that form complexes with the other active pharmaceutical ingredient such as calcium, iron or magnesium; sympathomimetic drugs and sympatholytic drugs; parasympathomimetic drugs and parasympatholytic drugs; antibodies that bind drugs; drugs to treat the side effects of the other active pharmaceutical ingredient without counteracting the effect of the other active pharmaceutical ingredient. Additionally or alternatively, the sheet like preparation may comprise, in a similar manner, a first layer with the active pharmaceutical ingredient and a second layer with the further active pharmaceutical ingredient that counteracts the active pharmaceutical ingredient of the first layer. In this case, the above mentioned advantages may be achieved, wherein the effect of the active pharmaceutical ingredient of the first layer is directed in the direction of the mucous membrane or away from it.

A preferred embodiment of the pharmaceutical dosage form according to the present invention is adapted for the application to an upper gastrointestinal tract such as throat, esophagus, cardia and/or stomach, and particularly to the respective mucous membranes and/or preferably to a buccal and/or esophageal mucosa.

A preferred embodiment of the pharmaceutical dosage form according to the present invention is adapted for the application to a nasopharyngeal mucosa.

In a preferred embodiment of the pharmaceutical dosage form according to the present invention, in particular a dosage form for the application to a buccal and/or esophageal mucosa, the shape of the dosage form or a part of the dosage form, in particular the shell, is such that can be swallowed.

In particular, a shell with the shape of a capsule can be swallowed. Preferably, the circumference of the capsule is shorter than 6 cm, preferably shorter than 3 cm, and preferably shorter than 2 cm, as well as longer than 0.2 cm, preferably longer than 0.5 cm, and preferably longer than 1 cm. Preferably, the longitudinal axis of the capsule is shorter than 5 cm, preferably shorter than 3 cm, and preferably shorter than 2 cm, as well as longer than 0.5 cm, preferably longer than 1 cm, and preferably longer than 1.5 cm. In particular, the shell may have a shape according to a standard capsule form such as 00, 0, 1 or 3, which have a length along the longitudinal axis between 16.1 mm and 23.5 mm and a circumference between 17.9 mm and 26.7 mm. In a similar manner the pharmaceutical dosage form or the part of the pharmaceutical dosage form to be swallowed may be shaped. Furthermore, a smooth and/or glidable surface of the shell, the dosage form or the part of the dosage form may be beneficial to facilitate the swallowing.

This advantageously allows an oral administration of the pharmaceutical dosage form according to the invention. In particular, only the dosage form or the part of the dosage form, preferably the shell, with the suitable shape is swallowed. In this context it is to be understood, that parts of the dosage form may be adapted to be swallowed while other parts of the dosage form may not be adapted to be swallowed.

In a preferred embodiment of the pharmaceutical dosage form according to the present invention, in particular a dosage form for the application to a buccal and/or esophageal mucosa, a nasopharyngeal mucosa, a gastrointestinal mucosa, a rectal mucosa or a vaginal mucosa, the sheet like preparation comprises at least one active pharmaceutical ingredient selected from the group: diagnostics substances such as dyes or stains, analgesics, preferably NSAIDs, such as ibuprofen or flurbiprofen; local anesthetics such as benzocaine, butamben, dibucaine, lidocaine, oxybuprocaine or novocaine; antibiotics such as penicillin, amoxicillin or vancomycin; antiseptics such as 2,4-dichlorobenzyl alcohol, amylmetacresol or cetylpyridinium chloride; steroids such as corticosteroids, glucocorticoids, fluticasone, budesonide, clocortolone, perdesonide, hydrocortisone, clobetasonbutyrate, flumetason, fluprediden, hydrocortisone aceponate, hydrocortisone buteprate, hydrocortisone-17-butyrate, triamcinolonacetonid, amcinoid, betamethason-17,21-dipropionate, betamethason-17-valerate, desoximetasone, diflucortolon-21-valerate, fluocinolonacetonid, fluocinonid, fluticason-17-propionate, methylprednisolone aceponate, mometasonfuroat, pednicarbat or clobetasol-17-propionate; parasizides, which are also called parasiticides, such as mebendazole, albendazole, tiabendazole, diethylcarbamazine, diaminodiphenyl sulfone, benznidazole, ivermectin, pyrantel, praziquantel; fungicides such as nystatin, imidazole, triazole, thiazole, clotrimazole, ketoconazole or undecylenic acid; hexamethyl pararosaniline chloride, Amphotericin B, botulinum toxin, sucralfat, nitric oxide or nitric oxide forming agents such as isosorbide dinitrate or nitroglycerine, furanocoumarins, benzoic acid, citric acid, lactic acid, pH buffers, antacids, calcium carbonate, magnesium carbonate or aluminum carbonate. Additionally or alternatively, the sheet like preparation particularly can comprise an inflammation regulator such as montelukast, interleukin receptors or interleukin antibodies. Additionally or alternatively, the sheetlike preparation particularly can comprise beclomethasone dipropionate, budesonide or ciclesonide, which are particularly beneficial for asthma therapy. Additionally or alternatively, the sheetlike preparation particularly can comprise mesalazine, sulfasalazine or olsalazine, which are particularly beneficial for treating inflammatory bowel disease.

In particular, the sheet like preparation comprising a specific active pharmaceutical ingredient advantageously allows, preferably locally, treating a respective disease or infection. Thus, a specific active pharmaceutical ingredient may be applied to a respective application site, in particular a mucosa, and the local concentration and/or the therapeutic effect may be increased and/or side effects, in particular adverse reactions, may be reduced compared to a systemic application. In this context it is to be understood, that besides the local effect also a systemic effect may be possible, preferably by the uptake of the active pharmaceutical ingredient through the mucous membrane into the body.

Moreover, in a preferred embodiment the sheet like preparation may comprise different active pharmaceutical ingredients, wherein at least one active pharmaceutical ingredient is chosen such that it remains, at least essentially, localized at and/or within the mucous membrane while at least another active pharmaceutical ingredient is chosen such that it enters the body through the mucous membrane, thus in particular causing a systemic effect.

A preferred embodiment of the pharmaceutical dosage form according to the present invention is adapted to be orally administered. Therefore, the dosage form or a part of the dosage form, in particular the shell, is shaped a swallowable manner. Preferably, this dosage form is formed as described above. Furthermore, this preferred embodiment may comprise a drug as the active pharmaceutical ingredient or active pharmaceutical ingredients that is traditionally unsuitable for oral administration, in particular due to a small bioavailability, highly variable intra- or inter-individual plasma levels, degeneration or deactivation of the drug by digestive secretions and enzymes, dilution effects by intestinal fluids, poor resorbability, a high first pass effect and/or a very short length of stay at the absorption window. Among these drugs are, for example: proteins and peptides such as insulin, buserelin, calcitonin or desmopressin which is also called oesmopressin; hormones such as estrogen; as well as biotechnologically produced drugs such as antibodies, in particular rituximab.

In a preferred embodiment of the pharmaceutical dosage form according to the present invention, in particular a dosage form for the application to a buccal, intestinal, rectal or vaginal mucous membrane, the sheet like preparation provides, after its release by the release mechanism, a relatively large surface area. In particular, the sheet like preparation is adapted to come into contact with a relatively large surface area, preferably of the mucous membrane, preferably at the predetermined site of release or site of action, after its release by the release mechanism. Consequently and preferably, the sheet like preparation can cover a relatively large surface area of the mucous membrane, in particular relatively large in comparison to the volume of the sheet-like preparation and/or to the amount of active pharmaceutical ingredients. Some particular advantages have already been described above. In particular, an enhanced resorption of the active pharmaceutical ingredient contained in the sheet like preparation can be realized. Moreover in a preferred variant of this embodiment, in particular with a sheet like preparation with multiple layers, the release of the active pharmaceutical ingredient can be directed into the mucous membrane. Thus, the local concentration of the active pharmaceutical ingredient and/or the bioavailability and/or the rate of absorption and/or the local effect may be increased. Furthermore, the concentration of the active pharmaceutical ingredient in the fluids that are present near the mucous membrane may be decreased by a directed release, and therefore side effects may be reduced and/or the bioavailability and/or the local effect may be increased.

The term "relatively large" as used herein preferably refers to one thing being a larger than another thing and/or one thing being larger than such a thing or corresponding quantity would be in a traditional embodiment of this thing, wherein preferably the extent, spatial extent, length, area, volume, surface area, cross-sectional area, enveloping cross-sectional area, contact area, covering area, diameter, circumference, path length, size, amount, quantity, scope, capacity and/or average size or scope is larger by a factor of preferably at least 125%, preferably at least 200%, preferably at least 500%, preferably at least 1000%, and preferably at least 5000%. In particular, a relatively large surface area of a sheet like preparation according to the present invention is larger than the surface area of a traditional dosage form or its preparation. In particular, the surface area of a sheet like preparation according to the present invention can be relatively large in comparison to the volume of the sheet like preparation. In particular, an area, preferably surface area, can be compared with a corresponding volume. Preferably, an area is relatively larger than a volume, if the square root of the area is larger than the cube root of the volume, preferably by a factor of at least 125%, preferably at least 200%, preferably at least 500%, preferably at least 1000%, and preferably at least 5000%. Additionally or alternatively, a relatively large surface area of a sheet like preparation preferably refers to a surface area of the sheet like preparation that is larger than the surface area of a traditional dosage form or its preparation with the same amount of an active pharmaceutical ingredient, preferably by the above given factors. It is to be understood, that the surface area of the sheet like preparation is an, at least essentially, uninterrupted surface area, while, in particular, a powder may also comprise a large surface area that is, however, not an essentially closed surface, but rather a huge number of small surface areas of the individual particles of the powder. In particular, mutatis mutandis, this also holds true for a drug or an active pharmaceutical ingredient that is dissolved in a fluid. Especially, a contact with a relatively large surface area, in particular of a mucosa, means that the contact area and/or the area that is covered, in particular by a sheet like preparation, is larger than the area which would be in contact and/or covered by a traditional dosage form or its preparation. Especially, if the traditional dosage form would dissolve in a fluid, then this fluid may have a large contact area with their respective mucous membrane, but the surface area would not be an essentially uninterrupted surface area, as described above, and/or the concentration of the drug or active pharmaceutical ingredient in said fluid may be lower than the concentration in the sheet like preparation and/or or in the mucous membrane covered by the sheet like preparation and/or in a fluid filled gap between the sheet like preparation and the covered area of the respective mucous membrane.

In a preferred embodiment the pharmaceutical dosage form according to the present invention, in particular a dosage form for the application to a buccal, esophageal, nasopharyngeal, intestinal, rectal or vaginal mucous membrane, the release mechanism is adapted to release the sheet like preparation while moving along the mucous membrane. It is to be understood, that the sheet-like preparation may be released only partially while moving along the mucous membrane. It is also to be understood, that the pharmaceutical dosage form or only a part of the pharmaceutical dosage form, in particular the release mechanism and/or the sheet like preparation or a part of it, may move along the mucous membrane. Additionally, the release may take place only during a part of the movement. In particular, the movement may take place along a path, preferably a predetermined movement path, and preferably the sheet like preparation or a part of it is released along this path or a long a part of it. Furthermore, the movement may be an active movement or a passive movement.

The term "active movement" as used herein preferably refers to a movement that is actively performed by the dosage form or a part of it, preferably by an actuator or movement mechanism of the dosage form. Thus, in particular, the pharmaceutical dosage form or a part of it generates a force to perform the movement.

The term "passive movement" as used herein preferably refers to a movement that is caused by external forces and/or movements. In particular, in a passive movement the dosage form or a part of it is moved by external movements and/or forces. Preferably, such an external movement and/or force may be a gravitational force, a movement of a mucous membrane, a movement of fluids that are present at a predetermined trigger site, application site or site of action, a movement of muscles, in particular of muscles that are near or belong to an organ with a respective mucous membrane, or forces generated by those movements. Preferably, the organ can be an esophagus, wherein the muscles of the esophagus perform a movement, in particular when swallowing, and thus generate a force, preferably via the mucous membrane of the esophagus and/or via a fluid, particularly a liquid such as a beverage, water or saliva, wherein the force acts on the dosage form or a part of it when it is present within the esophagus or near to it, preferably in the oral region. Also preferably and/or alternatively, the organ can be a nose, a throat or a nasopharyngeal region, wherein air breathed through the nose or mouth moves the pharmaceutical dosage form or a part of it.

In particular, this advantageously allows the release of the sheet like preparation along an extended, particularly elongated or oblong, region of a mucous membrane. Preferably, the sheet like preparation can be released along a path of movement of the pharmaceutical dosage form or a part of it. This path is preferably predetermined by the structure and/or movement of the mucous membrane or organ and/or fluids contained in the lumen of said mucous membrane or organ. Therefore in a preferred variant, the active pharmaceutical ingredient can be released along an extended, particularly elongated or oblong, region and/or along a path of the mucous membrane. Consequently and preferably, a spatially extended region of the mucous membrane or the organ can be, in particular locally, treated. Moreover in an alternate or further refined preferred variant, the sheet like preparation can release the active pharmaceutical ingredient locally to said extended region and/or over a prolonged time. Another advantage may arise from the fact, that, when the sheet like preparation is released during the movement, the sheet like preparation can be aligned to the direction of the movement, in particular along the path of the movement. Specifically with a dosage form, wherein the sheet like preparation comprises a first and a second region, those regions can be arranged at different sections of the mucous membrane and/or the path of the movement. Besides that, in particular by releasing the sheet like preparation during a passive movement, the risk of injury may be reduced.

Specifically, an esophagus can be treated with an active pharmaceutical ingredient that is locally applied to its mucous membrane. So, in particular, the active pharmaceutical ingredient can be applied to an extended region of the mucous membrane of the esophagus. Moreover, the active pharmaceutical ingredient may act locally to the mucous membrane of the esophagus. Therefore, side effects due to systemic effect of the active pharmaceutical ingredients may be reduced and/or the local effect to the mucous membrane of the esophagus, in particular due to the locally increased concentration of the active pharmaceutical ingredient, may be enhanced. Moreover, when the sheet like preparation releases the active pharmaceutical ingredient locally and/or over a prolonged time, the therapeutic response may be improved, and in particular the local effect of the active pharmaceutical ingredient can be increased. Furthermore, in particular due to the spatially extended region of action, the necessity for a systemic administration may be reduced.

Even more specifically, esophagitis, particularly eosinophilic esophagitis, can be treated by such a pharmaceutical dosage form. Here, a drug, in particular the active pharmaceutical ingredient, may target the mucous membrane of the esophagus and/or may preferably be selected from the group comprising: steroids such as corticosteroids, glucocorticoids, fluticasone, budesonide, clocortolone, perdesonide, hydrocortisone, clobetasonbutyrate, flumetason, fluprediniden, hydrocortisone aceponate, hydrocortisone buteprate, hydrocortisone-17-butyrate, triamcinolonacetonid, amcinoid, betamethason-17,21-dipropionate, betamethason-17-valerate, desoximetasone, diflucortolon-21-valerate, fluocinolonacetonid, fluocinonid, fluticason-17-propionate, methylprednisolone aceponate, mometasonfuroat, pednicarbat or clobetasol-17-propionate; nitric oxide or nitric oxide forming agents such as isosorbide dinitrate or nitroglycerine, beclomethasone dipropionate, ciclesonide, pH buffers, antacids, calcium carbonate, magnesium carbonate or aluminum carbonate. Additionally or alternatively, the sheet like preparation particularly can comprise an inflammation regulator such as montelukast, interleukin receptors or interleukin antibodies.

In a preferred embodiment of the pharmaceutical dosage form according to the present invention, in particular a dosage form for the application to a buccal and/or esophageal mucosa and/or to a nasopharyngeal mucosa, the release mechanism comprises a string member, wherein the string member is expandable from a compact form to an expanded form. In particular upon activation of the release mechanism, the string member can expand or can be expanded by another part of the release mechanism or by an external movement and/or force, preferably a movement of fluids at a predetermined trigger site, a movement of a mucous membrane or gravitational force, to the expanded form. Preferably, the string member comprises the sheet like preparation. The string member may comprise the sheet like preparation in the compact form and/or in the expanded form. Alternatively and preferably, the sheet like preparation may be adapted to form the string member. Thus, the string member contains the active pharmaceutical ingredient. It is to be understood, that the string member may only partially comprise the sheet like preparation or that the sheet like preparation may only partially form the string member. Furthermore, only a part of the string member may convert from a compact form to an expanded form, while at least one other part of the string member remains in a compact form or an expanded form.

The term "compact form" as used herein preferably refers to a folded form, coiled form, rolled form, coiled up form or collapsed form. In particular, a sheet like preparation has a smaller spatial extent and/or exposes a smaller amount of its surface in a compact form than in a form that is not a compact form, particularly in an expanded form. Preferably, a sheet like preparation in a compact form is folded, collapsed, coiled, rolled, coiled up, compressed, lumped together or brought into a smaller format in another way. In particular, a sheet like preparation can have a predetermined size or spatial extent, when it is in a compact form.

The term "expanded form" as used herein preferably refers to an unfolded form, spread out form, opened up form, elongated form, stretched form or oblong form. In particular, a sheet like preparation has a greater spatial extent and/or exposes a greater amount of its surface in an expanded form than in a form that is not an expanded form, particularly in a compact form. Preferably, a sheet like preparation in an expanded form is unfolded, spread out, opened up, unrolled, uncoiled, opened, elongated, stretched, expanded or brought into a bigger format in another way. In particular, a sheet like preparation can have a predetermined size or spatial extent, when it is in an expanded form. Alternatively, the size or spatial extent of a sheet like preparation may depend on the conditions present and a site of action or application site, and thus may not be predetermined.

The string member advantageously allows releasing the active pharmaceutical ingredient, in particular to mucous membranes that enclose a rather small lumen or cavity such as the esophagus or nasal cavity. Furthermore, the compact form of the string member advantageously makes it possible to provide a relatively small pharmaceutical dosage form, in particular for oral administration, which facilitates swallowing the dosage form. Additionally, the string member may expand, in particular unfold, uncoil, unroll, stretch or elongate, to the expanded form, and thus enable the release of the active pharmaceutical ingredient to an elongated region of a mucous membrane, in particular a buccal and/or esophageal mucosa and/or a nasopharyngeal mucosa. In particular, it is beneficial that the exposed surface area and/or the length of the string member or of the sheet like preparation exposed to the environment, in particular the mucous membrane, is increased, when the string member expands, particularly elongates or stretches, from the compact form to the expanded form. By this advantageous way, the active pharmaceutical ingredient is protected in the compact form and/or the release of the active pharmaceutical ingredient is enhanced by a rather large and/or long contact area in the expanded form. An advantage of a preferred variant of this embodiment is the use of the string member to support and/or to transport the sheet like preparation, and thus particularly making it possible to choose different substances and compositions for the sheet like preparation. Another advantage of an alternative and preferred variant results from the fact that the sheet like preparation forming the string member, and thus particularly making it possible to reduce the number of components of the dosage form and preferably to simplify the manufacturing of the release mechanism and/or the sheet like preparation.

In a preferred embodiment of the pharmaceutical dosage form according to the present invention the sheet like preparation, in particular in an expanded form, is string shaped, cord shaped, strip shaped or tube shaped. Preferably or alternatively, the sheet like preparation is bendable.

In a further refined or alternate preferred embodiment of the pharmaceutical dosage form according to the present invention, the sheet like preparation is adapted to form, in particular in an expanded form, a string, cord, strip or tube. Preferably, the sheet like preparation is bendable such that it can convert from a compact form, in particular with a folded, collapsed, coiled, rolled or coiled up sheet like preparation that may preferably have a string like, cord like, strip like or tube like shape, to the expanded form.

In particular, this advantageously allows the application of the dosage form and the release of the sheet like preparation to a mucous membrane that embraces a rather small lumen, in particular with a small diameter, and/or the treatment of a mucous membrane or an organ with a mucous membrane that shows an adverse effect when larger regions of it are covered or its lumen or a part of it is obturated by the sheet like preparation. Specifically, such an adverse effect can be a gag reflex, a sneeze stimulus or the blockage of fluid such as liquid, water, intestinal fluids or air. Another advantage is a possibly simplified manufacture. Additionally and preferably, the spatial extent of the expanded form, in particular the length of the sheet like preparation in its expanded form, in particular along its longitudinal and/or elongation axis, can be substantially larger than the spatial extent of the compact form, in particular the maximum diameter of the sheet like preparation in its compact form. The term "substantially larger" as used herein preferably refers to a ratio greater than or equal to 3:1, preferably 6:1, preferably 10:1, preferably 20:1, preferably 30:1, in particular with respect to an aspect ratio, an area ratio or a volume ratio. It is to be understood that it may also be beneficial to limit the maximum spatial extension and thus ratio to preferably 200:1, preferably 100:1, preferably 60:1, and preferably 40:1. In such a manner, in particular in a case where the volume of the sheet like preparation stays constant, a minimum diameter along a cross-section, which is, at least essentially, orthogonal to the longitudinal axis of the sheet like preparation in its expanded form, can be ensured. On the other hand, in case of a sheet like preparation that is, at least in its expanded form, shaped as a tube with a relatively larger diameter, preferably with a diameter that corresponds to the diameter of the respective lumen enclosed by the respective mucous membrane, the mucous membrane can be covered to a larger amount as compared to a sheet like preparation with a smaller diameter, e.g. a string shaped sheet like preparation.

In a preferred embodiment of the pharmaceutical dosage form according to the present invention the sheet like preparation, at least in the expanded form, is longer than 5 cm, preferably longer than 10 cm, preferably longer than 30 cm, and preferably longer than 40 cm, and preferably shorter than 95 cm, preferably shorter than 70 cm, and preferably shorter than 50 cm. In this context it is to be understood, that a dosage form, and in particular a sheet like preparation, that comprises at least one end adapted to be held during swallowing requires a length of the sheet like preparation that is correspondingly longer compared to the numbers given above, preferably by at least 5 cm, preferably by at least 10 cm, and preferably by at least 20 cm. Thus, such a sheet like preparation may preferably have length of, at least essentially, 60 cm.

In this context and/or the present invention, the term "length" or terms relating to length such as "longer" or "shorter" preferably refer to a length measured along the longitudinal and/or an expansion and/or an elongation axis of a respective object, in particular of the sheet like preparation. Specifically, the length of a sheet like preparation in its expanded form, preferably elongated form, may be measured with a tape measure. More specifically, the sheet like preparation may comprise a first end and a second end and the tape measure, in order to measure the length of the sheet like preparation, may be guided along the sheet like preparation from said first end to said second end. In particular, when the respective object, e.g. the sheet like preparation, follows, at least essentially, a straight line, the length of the respective object is the length along this line. Specifically, if this length is the longest spatial extent, the direction of said straight line corresponds to the longitudinal axis.

In a preferred embodiment of the pharmaceutical dosage form according to the present invention the sheet like preparation has an area and/or surface area between 0.5 and 25 cm², preferably between 2 to 25 cm², preferably between 5 to 25 cm², preferably between 5 to 15 cm², preferably larger than 0.5 cm², and preferably smaller than 40 cm². Preferably the ration of the length of the sheet like preparation and the width of the sheet like preparation is between 40:1 and 400:1, or preferably 60:1 and 300:1, or preferably 80:1 and 200:1. Said width can be an average width of the sheet like preparation, measured, for example, perpendicular to the length of the sheet like preparation. Said ratio can be a ratio of the length of the sheet like preparation and a circumference, in particular an average, of the sheet like preparation, wherein said circumference can be, for example, twice the width of a sheet like preparation in the case of a strip-shaped sheet like preparation.

In particular, this is beneficial for the application to a mucous membrane. Specifically, the mucous membrane of an esophagus can be covered and/or locally treated by such a sheet like preparation comprising the active pharmaceutical ingredient. It is to be understood, that depending on the specific embodiment of the dosage form that sheet like preparation may, at least partially and preferably to a substantially large extent, cover the mucous membrane of the esophagus and/or may extend, at least partially and preferably to a substantially large length, along the longitudinal axis of the esophagus. Therefore in a preferred variant, the active pharmaceutical ingredient can be released on an extended region of the esophageal mucosa, and thus this extended region can be treated. Moreover, in an alternate or refined preferred variant with a sheet like preparation that does not dissolve immediately, but preferably dissolves in a time controlled manner and/or adheres to the mucous membrane, the active pharmaceutical ingredient can be released over a prolonged time, and thus, in particular, the therapeutic effect may be improved.

In a preferred embodiment of the pharmaceutical dosage form according to the present invention the release mechanism is an expansion mechanism, preferably elongation mechanism, adapted to expand the sheet like preparation by leveraging an external movement, force or pressure.

It is to be understood, that the external movement, force or pressure particularly can be present at a predetermined trigger site, application site or site of action. Thus, it may serve as a key stimulus for the trigger mechanism, too. Additionally or alternatively, the external movement, force or pressure may expand the sheet like preparation in conjunction with the release mechanism. In this context, an external movement, force or pressure refers to a movement, force or pressure that is external to the pharmaceutical dosage form. Preferably, said movement, force or pressure is generated, at least partially, by the body of a person or animal to whom the pharmaceutical dosage form is administered, and thus is not external to said body. Therefore, such a movement can particularly be a passive movement. Preferably, such an external movement is a movement of a mucous membrane, a movement of fluids that are present at a predetermined trigger site, application site or site of action, a movement of muscles, in particular of muscles that are near to or belong to an organ with a respective mucous membrane, a peristaltic movement or a swallowing movement. In particular, the dosage form or a part of it may, preferably passively, move relative to the body of a user, in particular to a mucous membrane or organ. Preferably, such an external force can be caused by said external movements or is a force generated by a fluid surrounding the dosage form, a force generated by a mucous membrane, which is in particular in contact with the pharmaceutical dosage form or a part of it, a force generated by muscles that are near to all belong to an organ with a respective mucous membrane. Preferably and in a similar manner, such an external pressure can be caused by said external movements or can be a pressure of a fluid surrounding the pharmaceutical dosage form, in particular generated by a respective mucous membrane or corresponding muscles, or a pressure directly applied to the dosage form or a part of it, in particular by a respective mucous membrane or corresponding muscles, in particular by a gastrointestinal wall. It is to be understood, that additionally a gravitational force may act on the dosage form and parts of it, and therefore may improve, increase, decrease, hamper or facilitate said external movement, force or pressure. Specifically, a buoyancy force may be regarded as an external force and/or utilized for the expansion of the sheet like preparation.

Specifically, in case of an orally administered dosage form preferably for the application to the esophagus, the external movement may be the movement of the dosage form while it is swallowed. Therefore, the muscles of the esophagus generate a force that acts on the dosage form or a part of it. In particular, the mucous membrane of the esophagus can act directly on the dosage form and/or can act indirectly to the dosage form, preferably via a fluid, particularly a liquid such as a beverage, water or saliva, which is preferably swallowed together with the dosage form. Out of those movements forces or pressures may arise. From another point of view, forces and/or pressures of the esophagus, its mucous membrane and muscles may cause said movements. In particular, the change of pressure of a swallowed fluid can be used as a key stimulus for the trigger mechanism. Therefore, the expansion of the sheet like preparation may be improved and/or the release mechanism may be simplified. Preferably, the release mechanism can essentially passively release the sheet like preparation; so, the expansion of the sheet-like preparation takes place without generating an additional force by the pharmaceutical dosage form. Thus, an active release mechanism comprising an energy storage, e.g. a gas forming agent or a spring, is not required or, at least, the energetic requirements for a release mechanism, which only partially facilitates the passive expansion, reduced. Furthermore, this preferred embodiment, in particular, allows a release of the sheet like preparation during the swallowing of the dosage form. Finally, the costs for manufacturing may be reduced, the safety may be increased, the user convenience may be enhanced and/or the reliability may be increased.

An advantage of a preferred embodiment that leverages an external movement, force or pressure and the pharmaceutical dosage form can be particularly a reduced risk of injury, and increased safety, an improved user convenience and/or a reduced manufacturing cost. Preferably, the risk of injury can be reduced because the required movement, force or pressure to expand the sheet like preparation is external, and thus not generated by the dosage form, but rather, in particular, by the body of a user itself. Additionally or alternatively, also the manufacturing may be simplified because the release mechanism, preferably expansion mechanism, does not have to generate the required force, movement or pressure by itself but rather utilizes the external movement force or pressure, and thus corresponding additional structures and/or parts can be spared.

Additionally or alternatively, the leveraging of an external movement, force or pressure to expand the sheet like preparation may be advantageously combined with the release of the sheet like preparation while moving along the mucous membrane. In particular, this combination can release the sheet like preparation, at least partially, along its path of movement and this release is facilitated or is completely performed by utilizing just exactly this movement. Therefore, the manufacture may be simplified, the costs may be reduced, the safety may be increased, the user convenience may be enhanced and/or the reliability may be increased.

In a preferred embodiment of the pharmaceutical dosage form according to the present invention the release mechanism and/or the trigger mechanism is formed, at least partially, by the sheet like preparation. This may advantageously allow a simplified construction and/or manufacture. In particular, the manufacturing costs can be reduced. Preferably, the reliability of the pharmaceutical dosage form can be enhanced, particularly due to a reduced number of parts.

In a preferred embodiment of the pharmaceutical dosage form according to the present invention the pharmaceutical dosage form in particular the shell, contains the sheet like preparation in a compact form, preferably a folded, collapsed, coiled, rolled or coiled up form, and the release of the sheet-like preparation by the release mechanism, in particular expansion mechanism, preferably elongation mechanism, results in an expansion, preferably an unfolding, unwinding, stretching or elongation, of the sheet like preparation, in particular to an expanded form. This especially provides for the advantages described above regarding the compact and/or the expanded form. In particular, an elongation along an axis or movement path, preferably along the longitudinal axis of the sheet-like preparation in its expanded form, advantageously allows the release of the active pharmaceutical ingredient over an oblong region of a mucous membrane as well as a small dosage form compared to said oblong region, and thus preferably an orally administrable dosage form.

In a preferred embodiment of the dosage form according to the present invention the trigger mechanism is a holding device that is a part of or is attached to the sheet like preparation. In particular, this is beneficial to keep, at least a part, preferably an end, of the sheet like preparation and/or string member in a fixed position, while other parts of the sheet like preparation or of the dosage form move. Preferably, the holding device is adapted to be fixed, in particular the attached, positioned or mounted, to a predetermined region or part of a body of the user or a predetermined position. Furthermore, a force acting on the holding device may serve as a key stimulus. Especially, an external movement, force or pressure that acts on the pharmaceutical dosage form may cause such a force acting on the holding device. It is to be understood, that the holding device may also be attached to the sheet like preparation in an indirect way. In particular, the sheet-like preparation may transmit a force to the holding device, and vice versa, by another part of the pharmaceutical dosage form. Especially it is to be understood, that the string member or a part of it may form the holding device.

In a preferred embodiment of the dosage form according to the present invention, in particular a dosage form for the oral administration, the trigger mechanism, in particular the holding device, is adapted to be fixed in an oral cavity, preferably to a tooth, to a tongue, a lip or to an oral mucous membrane. Additionally or alternatively, the trigger mechanism is adapted to be held in a hand, preferably of a user, during swallowing of the pharmaceutical dosage form.

In particular, this advantageously allows ensuring a desired position of the trigger mechanism, preferably holding device, especially during the administration, e.g. swallowing, of the pharmaceutical dosage form. Preferably, in this manner, a position of the trigger mechanism, in particular holding device, can be predetermined for the application. Preferably and alternatively, the position of the trigger mechanism can result out of a random attaching, in particular, to a region of the respective mucous membrane. Specifically, the trigger mechanism, preferably holding device, can have adhesive properties and then, before swallowing of the pharmaceutical dosage form, randomly attach to a region of a buccal mucous membrane or a tongue. This is particularly advantageous, because a user may simply put the pharmaceutical dosage form into the mouth and then, preferably with a liquid, swallow it, wherein the trigger mechanism, preferably holding device, is attached in the oral cavity without further and/or specific action of the user.

The term "holding device" as used herein preferably refers to a device that is adapted to hold itself, and possibly further parts that are connected to it, e.g. a part of a sheet like preparation, at a defined position. In particular, a holding device is a handle, sling or adhesive tape or comprises an adhesive region. Moreover, the holding device may be adapted to build up and maintain a connection that can transfer a force between the holding device and a region where it is attached. Furthermore, this connection may be built up or maintained, while the dosage form and/or the sheet like preparation is in its compact form and/or its expanded form. Preferably, the holding device may hold itself, and possibly further parts, at a defined position or region by a force fit, in particular in a frictionally engaged manner, form-fittingly or by material engagement, in particular by mucoadhesion, preferably by an adhesive bond.

An advantage of such a holding device may arise from the fact, that a force acting on and/or a movement of the pharmaceutical dosage form can be used as a key stimulus for the trigger mechanism, wherein preferably the holding device is or is a part of the trigger mechanism, to trigger the release of the sheet like preparation. Preferably, an embodiment according to the invention with a holding device can be advantageously combined with utilizing external movement, pressure or force to expand the sheet like preparation. In particular, an external movement and/or force can serve as a key stimulus for the trigger mechanism, wherein the trigger mechanism preferably triggers the release of the sheet like preparation by the release mechanism, and then said external movement, force or an external pressure is utilized to expand the sheet like preparation, preferably by the release mechanism. Particularly this is the case, when the dosage form according to the present invention passively moves relative to the position where the holding device is fixed. Also preferably, embodiments with a holding device and/or leveraging an external movement, force or pressure can be advantageously combined with the release of the sheet like preparation during a movement of the dosage form or a part of it along the mucous membrane. In this case, a controlled and/or targeted triggering of the release may be achieved, a release and/or contact of the sheet-like preparation at the desired region of the mucous membrane may be ensured and/or due to utilizing the external movement, force or pressure the release mechanism may be simplified, manufacturing costs may be reduced, user convenience may be enhanced and/or the safety may be increased.

In certain embodiments fixing the holding device in the oral cavity can increase the user convenience. Furthermore, a holding device that is adapted to be fixed in the oral cavity may be manufactured in a simple, and thus cost efficient way, and/or may be particularly reliable, especially because the user may notice whether the holding device is properly fixed before continuing with the administering of the dosage form, e.g. swallowing the dosage form or a part of it. Similar advantages may arise for a holding device adapted to be held in a hand while administering of the dosage form.

In a preferred embodiment of the pharmaceutical dosage form according to the present invention, at least during the release of the sheet like preparation, the released portion of the sheet like preparation and the pharmaceutical dosage form move relatively to each other and thereby define a movement path of the dosage form. Additionally, when viewing in the direction of the movement path, the enveloping cross-sectional area of the dosage form is larger than the enveloping cross-sectional area of the sheet like preparation. In particular, the enveloping cross-sectional area of the dosage form can refer to the enveloping cross-sectional area of a swallowable part of the dosage form, preferably the shell. In particular, the enveloping cross-sectional area of the sheet like preparation can refer to the enveloping cross-sectional area of the released part of the sheet like preparation. It is to be understood, that these relations particularly hold true during the release of the sheet like preparation. In particular, the sheet like preparation may expand, and thus have a larger enveloping cross-sectional area than the dosage form afterwards. It is to be understood, that the above described relations are particularly important for the portion of the sheet like preparation that just has been released by the dosage form. Preferably, the length of this portion, measured along the movement path, is, at least essentially, as long as the length of the dosage form, measured along the movement path, preferably twice as long, preferably five times as long, and preferably twenty times as long. Particularly, the relation of enveloping cross-sectional areas can be reflected and/or correspond to the relation of the respective maximum diameters or minimum diameters, which follow the respective transverse axis or are, at least essentially, orthogonal to the respective longitudinal axis or direction of the movement.

This may advantageously allow facilitating the movement of the dosage form by swallowing it or by peristaltic movements. Certain variants of this embodiment can improve the user convenience and/or reduce the risk of injury. In particular, as at least a section of the released sheet like preparation that is next to the dosage form has a smaller cross-sectional area, such a dosage form is better a swallowable. Specifically, this tapering behind the dosage form helps the muscles of the esophagus to swallow the dosage form. Preferably, the dosage form, in particular the shell such as a capsule, also tapers at least in and/or against the direction of the intended movement path, and thus further facilitates swallowing it. Furthermore, the dosage form may be adapted such that its longitudinal axis is, at least essentially, parallel to the intended to movement path. Moreover, the dosage form may release the sheet like preparation against the direction of the intended movement path, e.g. at the rear side of the dosage form regarding to the intended movement path or movement of the dosage form.

In a preferred embodiment of the pharmaceutical dosage form according to the present invention the sheet like preparation has at least a first portion and a second portion with different enveloping cross-sectional areas, in particular when viewed in the direction of the movement path, wherein the portion that is released before the other portion has a smaller cross-sectional area. In an alternate and preferred embodiment the sheet like preparation tapers from a second end of the sheet like preparation to the first end of the sheet like preparation, wherein the first end of the sheet like preparation is on the side of the sheet like preparation that is released first. In particular, for the application to the esophagus both embodiments result in a sheet like preparation that is, after its release, smaller in the upper region of the esophagus and the oral cavity and larger in the lower region of the esophagus. This may beneficially facilitate the swallowing the dosage form and/or increase the user convenience, in particular suppress or avoid a gag reflex. In a preferred variant the first portion is a string member.

It is to be understood, that the terms "pharmaceutical dosage form" and "dosage form" as used herein are preferably interchangeable. Preferably, a dosage form can have non-pharmaceutical applications. In particular, a dosage form can be used for the therapy and/or for the diagnosis of a disease.

It is to be understood, that certain embodiments of a pharmaceutical dosage form according to the present invention differ from a catheter in that they are, at least essentially, fully enclosed by the body of a user after the administration. Additionally or alternatively, the administration is performed without additional tools and/or without applying a force or movement that is external to the body of a user. Preferably, a pharmaceutical dosage form according to the present invention can be administered by the user without professional help. This is particularly beneficial, if the dosage form is to be administered on a regular, in particular daily, basis. Furthermore, the user convenience may be improved, the safety may be increased and/or the risk of injury may be reduced. Especially, the convenient administration is also beneficial for the treatment of animals. Similarly it is to be understood, that a pharmaceutical dosage form according to the present invention is different from a stent. In particular, a stent does generally not comprise a trigger mechanism in the sense of the present invention. Moreover, the object of a stent generality is to keep open a hollow organ. Certain embodiments of a pharmaceutical dosage form according to the present invention may also keep open a hollow organ, however besides the object of keeping open a hollow organ their object is at least to improve the local application of a drug, particularly an active pharmaceutical ingredient. Some of the other embodiments of a pharmaceutical dosage form according to the present invention have the object to improve the local application of a drug, in particular an active pharmaceutical ingredient, and to let a hollow organ close, in particular even during the application of the dosage form. Particularly, this may be a achieved by a pharmaceutical dosage form comprising a string member or a sheet like preparation that is, in particular in an expanded form, string shaped, cord shaped, strip shaped or tube shaped. In particular, this is especially advantageous for the treatment of the esophagus.

In a preferred embodiment of the pharmaceutical dosage form according to the present invention the pharmaceutical dosage form, in particular the shell, comprises at least one aperture, and is adapted to release the sheet like preparation by passing it through the at least one aperture. A preferred variant of this embodiment advantageously protects the sheet like preparation by containing it in the shell. Furthermore, the reliability of a dosage form releasing the sheet like preparation through the aperture may be increased. Additionally or alternatively, the administration may be improved; in particular the user convenience may be enhanced, because the aperture may advantageously allow the controlled and/or directed release of the sheet like preparation.

In a preferred embodiment of the pharmaceutical dosage form according to the present invention comprising at least one aperture the trigger mechanism and the sheet like preparation are, at least partially, on opposed sides of the at least one aperture. Preferably, the trigger mechanism is not or only partially contained in the shell of the dosage form.

Preferably, the sheet like preparation is, at least partially, contained in the shell of the dosage form. This may improve the reliability and/or user convenience of the pharmaceutical dosage form. In particular, the storability can be improved. Besides that, this may advantageously allow to trigger the trigger mechanism with a key stimulus that is external to the dosage form and does not have to be transferred into an inner part of the dosage form, in particular into a shell of the dosage form. Moreover, the trigger mechanism may be exposed to the outside and thus be more sensitive to a possible key stimulus. Preferably, the trigger mechanism can comprise or is a holding device, which may be exposed to the outside and/or fixed in the oral cavity or held in a hand.

In a preferred embodiment of the pharmaceutical dosage form according to the present invention the release mechanism comprises or is an unwinding device that is adapted to release the sheet like preparation by unwinding it. This may advantageously allow releasing a sheet like preparation that is rolled, coiled or winded in its compact form. Furthermore, such an unwinding device may be conveniently formed by the sheet like preparation or a part of it, preferably by forming a coil. Preferably, such a coil may be supported with a rod, which may improve the ability to unwind it.

In certain embodiments of the pharmaceutical dosage form according to the present invention the sheet like preparation is in a solid-state, in particular while it is in its compact form and/or immediately after its release. This may beneficially enhance, enable or facilitate some of the above mentioned advantages. In particular, this may enhance the storability, when it is in a solid state prior the release. In particular, this may enhance and/or enable a targeted and/or sustained release of the active pharmaceutical ingredient, when it is in a solid state after its release. Additionally or alternatively, in certain embodiments of the pharmaceutical dosage form according to the present invention the sheet like preparation is adapted to dissolve, e.g. bio-degenerate, immediately, after a delay, in a time controlled manner or upon a stimulus after its release. This may beneficially enhance, enable or facilitate some of the above mentioned advantages. In particular, this can improve the user convenience, because the sheet like preparation does not need to be removed.

All embodiments of the pharmaceutical dosage form according to the present invention show the advantage that a pharmaceutical dosage form is provided in which the bioavailability of the active pharmaceutical ingredients contained in the administered dosage form is improved or in which, in particular additionally or alternatively, the local effect of the active pharmaceutical ingredient is improved. Additionally, by means of a pharmaceutical dosage form according to the present invention a dosage form is provided in which the release of the active pharmaceutical ingredient at its predetermined site of action is improved. Further advantageous of the pharmaceutical dosage form according to the present invention are:

Equal effect possible at lower dosages
Reduction of side effects due to a low dosage
Faster onset of effect by direct contact with the application site.

Exemplary embodiments of the present invention will be described in greater detail below with reference to the accompanying drawings and samples, from which further features, advantages, and embodiments can be learned.

Figure 2:
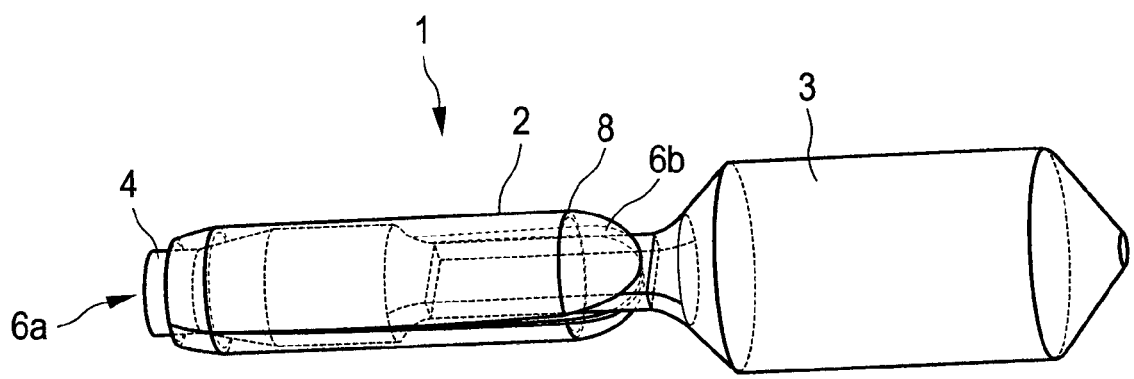
FIG. 2 shows a schematic perspective illustration of a pharmaceutical dosage form according to the invention in accordance with the first embodiment of the invention in a state after the release of the sheet-like preparation by the release mechanism.

In FIG. 1 a schematic perspective illustration of the pharmaceutical dosage form 1 according to the invention in accordance with a first embodiment of the invention in an initial state is shown. FIG. 2 shows the pharmaceutical dosage form 1 from FIG. 1 in a state after the release of the sheet-like preparation 3 by the release mechanism 4. In FIGS. 1 and 2 it can be seen that the illustrated pharmaceutical dosage form 1 comprises, in particular for the oral administration, a capsule-shaped shell 2, the shell contains a sheet-like, in particular film-shaped, foil-shaped or wafer-shaped preparation 3 comprising the active pharmaceutical ingredient in form of a folded, respectively unfoldable wafer 3, as well as a release mechanism 4 and a trigger mechanism 5 that is adapted to trigger the release of the sheet-like preparation 3 by the release mechanism 4 at a predetermined site of action, in particular of the gastrointestinal tract. The shell 2 comprises an aperture 6a on the one side an aperture 6b on the opposite side of the dosage form 1, in particular the aperture 6b is formed as a slit. The aperture 6a is covered by a trigger mechanism 5. When this aperture, at the site of action, is contacted with fluid surrounding the dosage form there, it dissolved and fluid can come into contact with the inner space 7 of the shell 2. The aperture 6a is at least partially covered by the trigger mechanism 5, e.g. a soluble polymer, which is adapted to trigger the release of the sheet-like preparation 3 by the release mechanism 4 after contacting the pharmaceutical dosage form 1, in particular the trigger mechanism 5, with a key stimulus. Here, a predetermined change of a physical or chemical parameter or a fluid surrounding the dosage form 1, in particular gastric juice in the stomach, or alternatively also fluid of the small intestine, which has a substantially lower pH value compared to the oral cavity and pharyngeal cavity, serves as a key stimulus to trigger the trigger mechanism 5. The trigger mechanism 5 is made of a substance whose solubility and/or solidity depends on the pH value that is present in the stomach.

In FIG. 2 the trigger mechanism 5 is not shown any more because it has already dissolved. The shell 2 is made of a material that is essentially insoluble in the gastric juice, e.g. hard gelatin or starch that is additionally coated with other polymers in order to remain stable in the gastric juice, which are stable on their own (e.g. Eudragit etc.). The release mechanism 4 is embodied as an expansion mechanism 4 that comprises a wick system, more specifically the gas driven expansion system, to which fluid is directed through the wick system by capillary forces. An expansion of the expansion mechanism 4 can result in an opening of the shell 2 at the predetermined breaking point 8 or is alternatively suitable to rupture a coating sealing the aperture 6b. This coating protects the dosage form 1 from an unwanted entry of fluid through the aperture 6b in an initial state. The latter can be seen in the interplay between FIG. 1 and FIG. 2. Preparation 3 is contained in the shell 2 in a folded form that is shown in FIG. 1, wherein—as shown in FIG. 2—the expansion of the expansion mechanism 4 results in an unfolding of the preparation 3, wherein the preparation 3 escapes through the slit 6b and inflates like a balloon. For this purpose, a gas-forming agent, e.g. a powder that optionally can be incorporated into a wick system, in particular comprising capillaries e.g. fibers, that can absorb a fluid, is arranged in the area of the shell 2, that is shown in FIGS. 1 and 2 on the left hand side, as a release mechanism 4 and expansion mechanism 4. For example, sodium hydrogen carbonate or citric acid or alternatively a pressurized gas is suitable as a gas-forming agent, here.

In particular, a release mechanism and the expansion mechanism is formed in such a way that the formed gas is directed only into the wafer respectively balloon 3 and cannot escape at another place. At the time of release, the powdery gas-forming agent and the wick system 4 are kept in contact. Therefore it is beneficial when the gas-forming agent is incorporated into the wick system.

In case of a liquid or partial liquid gas-forming agent, a separated compartment may contain the gas-forming agent, that compartment is at least partially formed out of the outer shell 2 of the dosage form. Thus, the gas-forming agent is arranged in a part of the shell 2 that is opposed to the part of the shell by containing the preparation 3—arranged at the right hand side of the shell in the figures. The gas-tight shell 2 which can be filled with a gas comprises a central aperture 6a that is circumferentially attached at an inner edge of the shell 2. After triggering of the release mechanism, liquid is directed to the release mechanism in form of a gas-forming agent through the wick system 4 and gas is formed by the gas-forming agent and is directed into an inner space of the sheet-like preparation 3. For this purpose, this preparation is formed as a gas-tight shell that can be filled with a gas, in particular a balloon, as in particular shown in FIG. 2.

In FIG. 1 the preparation 3 formed as a gas-tight gas-fillable shell is present in folded form. Furthermore, it can be seen from FIG. 1 that the shell is divided at its periphery. It is also seen from FIG. 1, that the shell comprises at least one predetermined breaking point. It is to be understood that, depending on the actual embodiment, it can be sufficient that the balloon 3 protrudes through the slit 6b only. However, further experiments have shown that in order to completely unfold the balloon a predetermined breaking point 8 at the shell 2 may completely rupture or fold open, in particular by the gas pressure developed in the balloon 3. In particular, such a mechanism can be held together by a coating of the slit 6b in the initial state. Such a coating may also be chosen such that it—in particular when it is chosen from a similar or from the same material as the trigger mechanism 5, this coating is etched or dissolved at the trigger site, respectively site of action, such that gas pressure can open up the capsule 2. For this purpose, it may be beneficial, that the coating of the slit 6b dissolves more slowly than the trigger mechanism 5. It is to be understood that just one predetermined breaking point 8 or a folding mechanism at this position may be provided or just a slit 6b or a combination thereof may be provided in different actual further embodiments. The actual embodiment may be chosen by a person skilled in the art depending on the size and scope of application and depending on the actually used materials.

Gastric juice or intestinal fluid enters at the predetermined trigger site, here e.g. in a stomach or in the intestine, the inner space 7 of the shell through the aperture 6a and results in a formation of gas by the gas-forming agent. Along with this gas is directed into the inner space of the wafer 3 which inflates like a balloon at the site of application and expands. Along with this the capsule-shaped shell 2 is opened at one of its—here right end—by e.g. the breaking of the predetermined breaking point 8 by the pressure of the expanding balloon 3 and/or by protruding of the balloon 3 through the aperture 6b. In this way, a complete unfolding and release of the wafer 3 of the capsule 2 is possible. In particular, such a construction allows forming a relatively large wafer surface which can rest over a relatively large area of the gastric wall in order to release the active pharmaceutical ingredient. Alternatively and in particular, such a construction allows forming a relatively large wafer surface which can rest over a relatively large area of the intestinal wall in order to release the active pharmaceutical ingredient. It is also to be understood that a part of the wick system 4 may stick out of the shell and direct the fluid into the inner space of the shell 2. The portion of the wick system 4, which is located outside the shell, is expediently covered by the release mechanism 5 in an initial state, and released upon activation.

Figure 3:
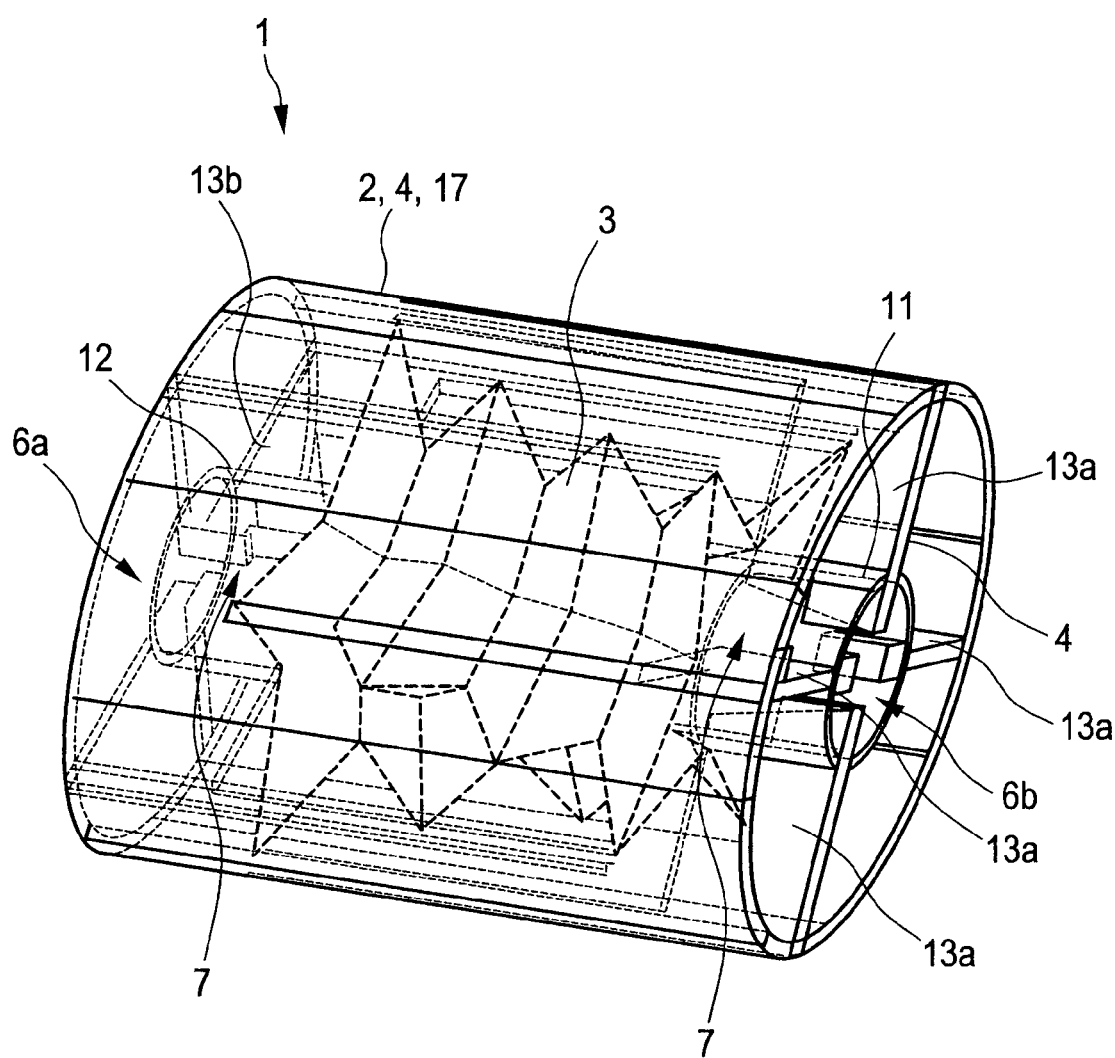
FIG. 3 shows a schematic perspective illustration of a pharmaceutical dosage form according to the invention in accordance with a second embodiment of the invention in an initial state.

FIG. 3 shows a schematic perspective illustration of a pharmaceutical dosage form 1 according to the invention in accordance with a second embodiment of the invention in initial state. Again, the pharmaceutical dosage form 1, which is, in particular, suitable for oral application, comprises a shell 2 wherein the shell 2 contains a sheet-like, in particular film-shaped, foil-shaped, or wafer-shaped preparation 3 comprising the active pharmaceutical ingredient in form of a folded wafer 3 as well as a release mechanism 4 and a trigger mechanism 5 that is adapted to trigger the release of the wafer 3 by the release mechanism 4 at a predetermined site of action, e.g. the gut. The shell 2 comprises a central aperture 6a, respectively 6b, at both sides that are closed by a coating, e.g. a dissolvable coating or something similar. After the application, the apertures 6a and 6b are covered, whereby the trigger mechanism 5 can come into contact with a fluid. However, an aperture does not have to be present, because the trigger mechanism may also be located at the circumference of the dosage form 1. The fluid of the gastrointestinal tract or the small intestine surrounding the shell 2 comes into contact with the inner space 7 of the shell after dissolution of the coating. The trigger mechanism 5 is adapted to trigger the release of the sheet-like preparation 3 by the release mechanism after contacting the pharmaceutical dosage form, in particular of the trigger mechanism 5, with a key stimulus. For example, in the illustrated embodiment, an action of pressure caused by an intestinal peristalsis or a specific pH value usually prevailing or occurring at the site of action serves as a key stimulus. In the illustrated embodiment, the trigger mechanism is formed by a soluble polymer that is located at the inside of the tube elements 11 and 12. In particular, an action of pressure can serve as a key influence if the levers of the capsule are held together with a material that breaks upon action of pressure. The release mechanism 4 is constructed as an expansion mechanism 4, specifically as a mechanical expansion system, wherein an expansion of the expansion mechanism 4 results in an unfolding of the wafer 3.

Figure 4:
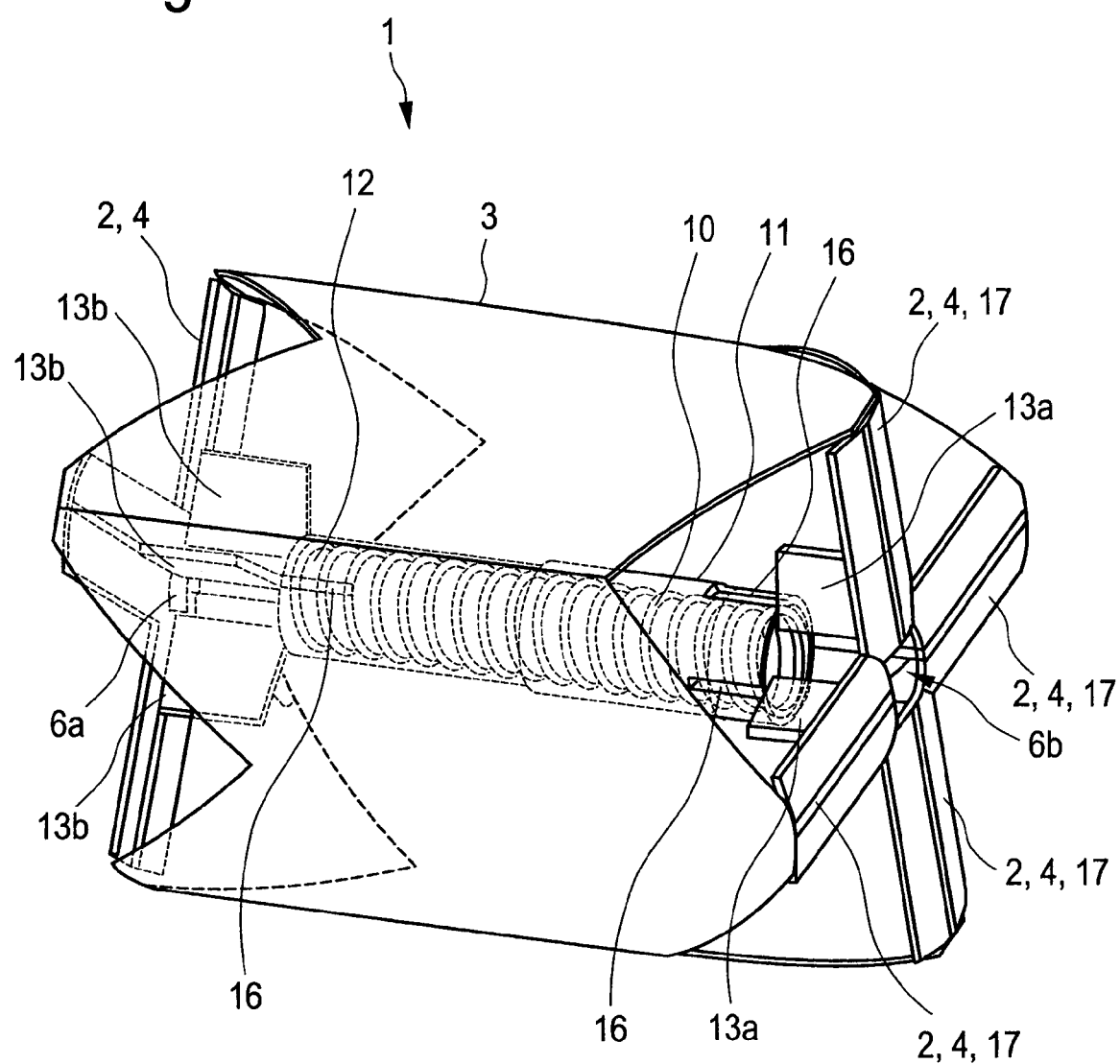
FIG. 4 shows a schematic perspective illustration of a pharmaceutical dosage form according to the invention in accordance with the second embodiment of the invention in a state after the release of the sheet-like preparation by the release mechanism.

FIG. 4 shows the embodiment illustrated in FIG. 3 in an unfolded state. The shown embodiment comprises, as part of the mechanical expansion system, a plurality of joint or lever elements 13, which are arranged at both free ends of the shell 2 in the area of the central aperture 6, as well as a spring element 10 that is arranged within the tube elements 11 and 12 that are slit into each other. In particular, the joint or lever elements 13a of the first tube 11 and the joint or lever elements 13b in in tube 12 are arranged alternately in a closed initial state of the dosage form 1 as shown in FIG. 3 such that in the closed state as shown in FIG. 3 the joint or lever elements 13a of the first tube 11 and the joint or lever elements 13b of the second tube form a shell 2, respectively a cladding, that is flipped open upon release and that opens up the preparation 3.

In particular, the length of the lever of the joint or lever elements 13a of the first tube 11 and of the joint or lever elements 13b of the second tube 12 have the whole length of the folded dosage form 1 in this arrangement. It is to be understood that in the case, in which the lever or joint elements 13a and 13b are arranged opposing each other, the maximum length of the lever is limited to half of the length of the dosage form 1. In this case, the first and the second tube element 11 and 12 as well as the lever and joint elements 13a and 13b are arranged such that the lever and/or joint elements 13a, respectively 13b, form a wreath structure and the lever and joint elements 13a at the tube element 11 and the lever and joint elements 13b at the tube element 12 are respectively attached in a slit at the tube element 11, respectively 12, when the dosage form 1 is viewed from the rear or from the front, thus looking on the smallest surface area of a dosage form 1. The resilient force of the spring 10 pushes the lever and joint elements 13a and 13b through this slit 16 to the outside, and the wafer 3 is unfolded as the cladding or shell parts 17 that are pivotally attached at the lever and joint elements 13a and 13b, respectively, swing outwards. In this context it is to be understood that the pivotally attached cladding or shell parts 17 may also form lever or joint elements and may be understood as such.

In such an arrangement, it is beneficial if, as shown in FIG. 3, in a closed state of the dosage form 1 the cladding or shell parts 17 of the first tube 11 forming joint or lever elements and the cladding or shell parts 17 of a second tube 12 forming joint or lever elements are arranged alternately such that preferably in a closed state, the cladding or shell parts 17 of a first tubel 1 forming joint or lever elements and the cladding or shell parts 17 of the second tube 12 forming joint or lever elements form the shell and/or the cladding 2. The wreath structure at a first end of the dosage form 1, in particular at an end of the first tube element 11, and the wreath structure at a second end of the dosage form 1, in particular at an end of the second tube element 12, are offset in a rotationally symmetric manner. A joint or lever movement of the joint elements 13a and 13b cause an unfolding of a sheet-like preparation 3, that is folded in an initial state in the dosage form 1, by the spring force driven movement in the slit 16 to the outside as the cladding or shell parts 17 swing outwards such that the sheet-like preparation 3 unfolds at a predetermined site of action in a particular advantageous manner, and preferably can contact a mucous membrane or the intestinal wall.

The shell 2 comprises the tube elements 11 and 12 that are pushed into each other by a spring 16 arranged in the tube elements 11 and 12 in such a way that they can move relatively to each other and that are centrally arranged in the main longitudinal axis of the dosage form 1. By the action of pressure of the intestinal peristalsis or the dissolution of a coating and the subsequent entry of fluid to trigger the release mechanism the mechanical expansion system is triggered and by means of the spring driven joint or lever elements 13a, 13b in combination with the shell or cladding elements 17 the unfolding of the wafer 3 and thus its release out of the shell is effectuated. In particular, this expansion thus can be assisted or directed by providing at least a further joint or lever element.

FIG. 5a, 5b show a schematic perspective illustration of a pharmaceutical dosage form 1 according to the invention in accordance with a third embodiment of the invention in an initial state and FIG. 5c shows a photograph of the pharmaceutical dosage form according to the invention in accordance with a third embodiment of the invention in an initial state. FIG. 5a shows the embodiment in a side view and FIG. 5b shows a view to the tip of the embodiment. This pharmaceutical dosage form 1 according to the invention is adapted for the application onto a mucous membrane, in particular onto a vaginal mucous membrane, but also onto a rectal mucous membrane, and comprises the sheet-like, in particular film-shaped, foil-shaped or wafer-shaped preparation 3 that comprises the active pharmaceutical ingredient in form of a wafer 3 which is circumferentially arranged at a longitudinal section of the cylindrical main body of the dosage form 1 that tapers on one side. In particular, the main body may be a tampon that is essentially formed out of a swellable material. This swellable material may form both, the release mechanism 4 and the trigger mechanism 5, which swells upon contact of the dosage form 1 with a fluid, in particular a vaginal fluid, and thus unfolds the preparation 3. Because of the increase of the diameter of the dosage form 1 due to the swelling, also the circumference of the preparation 3 increases. This is the case because the preparation 3 may be folded into grooves or depressions of the main body of the dosage form.

FIGS. 6a, 6b, and 6c show an alternative embodiment that defer from the embodiment shown in the FIGS. 5a, 5b, 5c in that here the preparation 3 is partially folded outwards. Due to swelling of the main body of the dosage form at a predetermined site of action, here, in particular, the rectum or preferably the vagina, the release of the sheet-like preparation 3 by the release mechanism 4 is triggered.

It is to be understood that the main body of the dosage form 1 may comprise grooves or may not comprise grooves depending on the embodiment.

In particular, however, a polymer being a glue can serve as a further trigger mechanism 5, wherein the polymer dissolves at least partially or completely upon contact with the fluid at the trigger site. In particular, such a polymer may attach the preparation 3 to the main body or may, additionally or alternatively, glue the foldings of the wafer 3 together. In particular, this may result in that the wafer 3 does not unfold as the polymer acting as a trigger mechanism 5 is not or is at least partially not dissolved. In the context of the embodiments shown in FIG. 5 and FIG. 6, it is also to be understood that these are particularly suited for embodiments in which a rapid and immediate release and dissolution and thus a relatively fast and immediate contacting of the wafer with the site of application, in particular of the vaginal mucous membrane, is intended.

Figure 7:
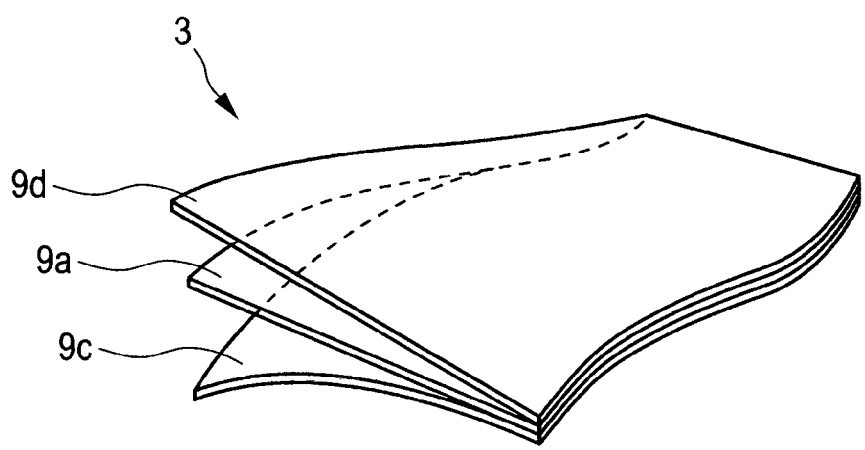
FIG. 7 shows the schematic structure of an example of a three-layered film-shaped preparation of the present invention.

FIG. 7 shows the schematic structure of a three-layered sheet-like preparation. A sheet-like preparation, like it is contained in the pharmaceutical dosage form 1 according to the invention, may have a thickness of 0.01 mm to 2 mm, preferably 0.03 mm to 1 mm, preferably 0.05 mm to 0.1 mm, wherein the sheet-like preparation 3 has an area between 0.5 and 20 cm², preferably between 1 and 10 cm². In particular, a sheet-like preparation 3 comprises at least one layer comprising an active pharmaceutical ingredient. The sheet-like, in particular film-shaped, foil-shaped or wafer-shaped preparation 3, which preferably has the shape of a wafer 3, contains an active pharmaceutical ingredient with an active ingredient content of 0.5 to 40% by weight, preferably 1 to 30% by weight, and more preferred 5 to 20% by weight. A sheet-like preparation 3 may have a single-layered or a multi-layered structure out of one or more layers 9, wherein at least one first layer 9a contains an active pharmaceutical ingredient. FIG. 7 shows the exemplary structure of a three-layered wafer 3 with a single layer containing an active substance 9a.

The dosage form according to the invention is further elucidated by the following examples.

EXAMPLE 1

The single-layered or multi-layered preparation according to the present invention preferably has a paper-like form.

The preparation according to the present invention dissolves preferably within 1 h, more preferably within 30 min, most preferably within 15 min and particularly most preferably within 5 min after contact with the site of action, in particular the mucous membrane.

They essentially comprise a mucoadhesive, active substance containing layer, which preferably comprises: mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, plasticizers such as polyethylene glycol, glycerol, sorbitol, and mixtures thereof, and solvents such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, lubricants, and mixtures thereof may be contained.

In particular, substances out of the following groups are suitable as active pharmaceutical ingredients: drugs acting on the skeleton and the muscles, drugs acting on the nervous system, hormones and drugs acting on the hormonal system, gynecological acting drugs, drugs acting on the cardiovascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides.

Development and Testing

In order to develop and test a preparation in the form of a wafer suitable for the present invention, testing methods based on the following test and selection protocol 1 have been conducted.

In this way, preparations are obtained that meet the requirements which arise, in particular, for a usage in connection with the dosage form.

In particular, the wafers according to the present invention are distinguished over previously known wafers by the fact that they do not dissolve at just a slight contact with fluid already and that they have a relatively high stretchiness and fracture resistance.

Testing and Selection Protocol 1

Development Film Formulation

Optical assessment:
- homogeneous appearance
- no inclusions of air bubbles ⟶ discard
- smooth surface       no ↓ yes

- Can the wafer be detached from the release liner well ⟶ discard
- Can the wafer be cut well       no ↓ yes Measurement
- layer thickness
- weight/cm²

↓

Disintegration time ⟶ discard
- in 10 mL of water     more than 120 sec
- on alginate film
(simulation of mucous membrane)

↓ less than 120 sec

Elasticity/Flexibility
- tensile strength (less than 0.005 Mpa)
- elongation until breaking = stretchiness (more thank 40%) ⟶ discard
- folding durability (more than 100)       no ↓ yes suitable for further development Especially for a vaginal, rectal or intestinal mucous membrane, a tensile strength of less than 3.5 MPa may be beneficial to increase the safety, the user convenience and/or to enable a close but flexible fitting of the sheet like preparation with the respective mucosa.

Especially for an esophageal mucous membrane and/or for the application to the esophagus, a tensile strength of more than 15 MPa may be beneficial, particularly for avoiding a rupture of the sheet like preparation during its application, especially during swallowing the dosage form.

Example 2—Single-Layered Preparation

Single-layered preparations, in particular wafers, that are suitable for the usage according to the invention, may, in particular, comprise the following formulations:

| A | 10% | PVA |
|---|---|---|
|   | 20% | PEG 400 |
|   | 5% | HPMC |
|   | x% | active pharmaceutical ingredient ad 100% demineralized water |
| B | 5% | PVA |
|   | 15% | Kollicoat® IR |
|   | x% | active pharmaceutical ingredient ad 100% demineralized water |
| or |  |  |
| C | 5% | PVA |
|   | 15% | Kollicoat® IR |
|   | 8% | Glycerol 85% |
|   | x% | active pharmaceutical ingredient ad 100% demineralized water |

Example 3—Two-layered Preparation

Two-layered preparations, in particular wafers, according to the present invention comprise a mucoadhesive layer containing an active substance and a water-impermeable layer, which is called a backing layer. The mucoadhesive layer containing an active substance is preferably composed of mucoadhesive polymers as cellulose derivates, starch and starch derivates, polyvinyl alcohol, polyethylene oxide, polyethylene, polypropylene, polyacrylic acid and polyacrylate derivates, polyvinylpyrollidone, Povidone, Copovidone, sodium alginate, gelatin, xanthan gum, guar gum, Carrageenan, pectins, dextrans, lectins, Chitosan, Pullulan an mixtures thereof, plasticizers such as polyethylene glycol, glycerol, sorbitol and mixtures thereof, and the solvent such as water, ethanol, methanol, acetone, organic solvents and mixtures thereof. Furthermore, additives such as colorants, fragrances, flavoring agents, preservatives, antioxidants, penetration enhancers, solubilizers, disintegration accelerators, lubricants, and mixtures thereof may be contained. Substances of the following group are suitable as active pharmaceutical ingredients: Drugs acting on the skeleton and on the muscles, drugs acting on the nervous system, hormones and drugs acting on the hormonal system, gynecological acting drugs, drugs acting on the cardio-vascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives and parasizides.

The backing layer preferably comprises an ethyl cellulose layer of varying thickness, wherein ethyl cellulose of different viscosities may be used. Furthermore, it is possible to incorporate further additives such as colorants, fragrances, flavoring agents, preservatives, antioxidants, solubilizers, pore formers, lubricants, and mixtures thereof.

Table 1 which follows shows various exemplary compositions of layers of a two-layered wafer 3 according to the present invention.

TABLE 1

| Adhesive layer containing an active substance | | | | | |
|---|---|---|---|---|---|
| PVA | 10% | 10% | 10% | 10% | 10% |
| PEG 400 | 20% | 20% | 20% | 20% | 20% |
| HPMC | 5% | 5% | 5% | 5% | 5% |
| Active pharmaceutical ingredients | x% | x% | x% | x% | x% |
| Water | ad 100% | ad 100% | ad 100% | ad 100% | ad 100% |
| Water-impermeable layer (backing layer) | | | | | |
| Ethyl cellulose 10 (4% solution in acetone) | 300 µg EC/cm$^2$ | 400 µg EC/cm$^2$ | 500 µg EC/cm$^2$ | 750 µg EC/cm$^2$ | 5000 µg EC/cm$^2$ |
| Ethyl cellulose 45 (4% solution in acetone | 300 µg EC/cm$^2$ | 400 µg EC/cm$^2$ | 500 µg EC/cm$^2$ | 750 µg EC/cm$^2$ | 5000 µg EC/cm$^2$ |

The sheet-like, in particular film-shaped, foil-shaped, wafer-shaped preparation 3 comprising the active pharmaceutical ingredient comprises at least one first layer 9a containing the active substance. The layer 9a containing the active substance preferably comprises a polymer, more preferably a film-forming polymer, wherein the polymer fraction in the layer 9a containing the polymer and the active substance is 10 to 90% by weight, preferably 20 to 70% by weight, and more preferred 30 to 60% by weight, and wherein the layer containing the active substance, in particular in a two-layered wafer, is an adhesive layer 9a, and wherein the polymer is a water-dispersible and/or water-decomposable and/or water-disintegrable film-forming polymer.

Furthermore, the sheet-like, in particular film-shaped or wafer-shaped preparation 3 comprising the active pharmaceutical ingredient comprises at least one active substance free layer 9c, that does not contain an active pharmaceutical ingredient. In a three-layered wafer 3 the wafer 3 comprises a further active substance-free layer 9d that also does not contain an active pharmaceutical ingredient. Such a first active substance free layer 9c and/or such a further active substance free layer 9d is preferably a water-insoluble layer, e.g. made of or comprising ethyl cellulose. An active substance free layer 9c and/or a further active substance free layer 9d may be formed as an adhesive layer, in particular in a two-layered wafer 3, wherein the layer consists of or comprises e.g. hydroxypropyl methylcellulose. In a multi-layered, in particular three-layered wafer 3 layer 9a containing the active substance is preferably arranged between two active substance free layers 9c, 9d, wherein a layer 9a containing the active substance may be arranged between a first active substance free layer 9c and a further active substance free layer 9d and wherein preferably the first active substance free layer 9c is a water-insoluble layer, which more preferably comprises ethyl cellulose, and wherein the at least one further active substance-free layer 9d is an adhesive layer, which more preferably comprises hydroxypropyl methylcellulose.

Example 4—Three-Layered Preparation

Three-layered preparations, in particular wafers, according to the present invention preferably comprise a mucoadhesive layer containing an active substance, a water-impermeable layer, which is called a backing layer, and an adhesive protective layer. The mucoadhesive layer containing the active substance may be composed of mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, plasticizers such as polyethylene glycol, glycerol, sorbitol, and mixtures thereof, and solvents such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, lubricants, and mixtures thereof may be contained. In particular, substances out of the following groups are suitable as active pharmaceutical ingredients: drugs acting on the skeleton and the muscles, drugs acting on the nervous system, hormones and drugs acting on the hormonal system, gynecological acting drugs, drugs acting on the cardiovascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides. The backing layer is made of an ethyl cellulose layer with a varying thickness, wherein ethyl cellulose with various viscosities may be used. Moreover, the incorporation of other additives such as colorants, fragrances, flavoring agents, preservatives, antioxidants, solubilizers, pore formers, lubricants, and mixtures thereof is possible. The adhesive protective layer may vary in its thickness and is made of mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, and a solvent such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, pore formers, lubricants, and mixtures thereof may be contained.

Table 2 which follows shows various exemplary compositions of layers of such a three-layered wafer 3.

TABLE 2

| Adhesive protective layer | | | | |
|---|---|---|---|---|
| HPMC (0.5% solution in water) | 50-100 μm layer | 50-100 μm layer | 50-100 μm layer | 50-100 μm layer |
| Mucoadhesive layer containing the active substance | | | | |
| PVA | 10% | 10% | 10% | 10% |
| PEG 400 | 20% | 20% | 20% | 20% |
| HPMC | 5% | 5% | 5% | 5% |
| Active pharmaceutical ingredients | x% | x% | x% | x% |
| Water | ad 100% | ad 100% | ad 100% | ad 100% |
| Water-impermeable layer (backing layer) | | | | |
| Ethyl cellulose 10 (4% solution in acetone) | 300 μg EC/cm$^2$ | 400 μg EC/cm$^2$ | 500 μg EC/cm$^2$ | 750 μg EC/cm$^2$ |
| Ethyl cellulose 45 (4% solution in acetone | 300 μg EC/cm$^2$ | 400 μg EC/cm$^2$ | 500 μg EC/cm$^2$ | 750 μg EC/cm$^2$ |

A sheet-like preparation 3 of a pharmaceutical dosage form 1 according to the present invention may also be formed out of one layer or out of multiple layers, in particular out of two layers.

Example 5

Regarding the Calculation of the Amount of Active Ingredient Per Wafer:

In particular, the amount of active ingredient based on the layer thickness of the wet polymer film can be calculated according to the following formula:

$$m(\text{active pharmaceutical ingredient}) = \frac{m(\text{formulation}) * m\left(\frac{\text{active pharmaceutical ingredient}}{\text{wafer}}\right) * 10000}{p(\text{polylmer mass}) * A(\text{wafer}) * h(\text{doctor blade})}$$

wherein
m mass [g]
p density [g/cm$^3$]
A area [cm$^2$]
h height [μm]

In this context it is important to keep in mind that the height of the doctor blade is not equal to the layer thickness of the wet wafer. Reasons for this are, for example, the shearing of the polymer film while it is spread out, the flowing apart or flowing together of the polymer composition after spreading out, and the formation of thicker regions at the edges of the polymer film. The extent of these processes is, inter a/ia, dependent on the viscosity of the polymer solution and on the used active pharmaceutical ingredient. Therefore, for each active pharmaceutical ingredient a specific individual fraction may be added to the calculated amount of active ingredient. This additional fraction is 35% for sodium fluorescein
40% for quinine
35% for sodium diclofenac Moreover, one may use a drug specific factor to adjust the calculated amount, wherein, in particular, the drug specific factor is 100%+the additional fraction, and therefore the formula reads:

$$m(\text{active pharmaceutical ingredient}) = \frac{m(\text{formulation}) * m\left(\frac{\text{active pharmaceutical ingredient}}{\text{wafer}}\right) * 10000}{p(\text{polylmer mass}) * A(\text{wafer}) * h(\text{doctor blade})} * \text{drug specific factor}$$

Example 6—Manufacture of Single-Layered Wafers

The manufacture of single-layered wafers is carried out by a solvent casting method, wherein at first all ingredients are dissolved in the solvent, homogenized, and subsequently spread out on a suitable release liner to the desired thickness using a doctor blade. Then, the resulting film is dried under defined conditions and then cut into pieces of suitable size.

In the following, the manufacturing methods for the preparations mentioned in Example 2 above are described in detail:

A At first, polyvinyl alcohol (PVA) is dissolved in demineralized water in a beaker at a temperature of 90° C. and at a stirring speed of 400 rpm. Then, polyethylene glycol 400 (PEG 400) and the medical substance or the medical substance solution, respectively, is added and the solution is homogenized. Finally, hydroxypropyl methylcellulose (HPMC) is added with stirring, homogenized, and the evaporation loss is compensated with demineralized water. The polymer solution is covered and left overnight and centrifuged on the next day at 4400 rpm for 50 min in order to remove air bubbles. Then, the solution is evenly spread out onto the release liner by means of a doctor blade and the polymer film is dried for 6 h at 40° C. in a drying cabinet. Before testing and further use, the film is cut into appropriately sized pieces and detached from the release liner. The single-layered wafer is stored on the release liner and is wrapped in aluminum foil.

B At first, polyvinyl alcohol (PVA) and Kollicoat IR are dissolved in demineralized water in a beaker at a temperature of 90° C. and at a stirring speed of 400 rpm. Then, the medical substance or the medical substance solution, respectively, is added, homogenized, and the evaporation loss is compensated with demineralized water. The polymer solution is covered and left overnight and is centrifuged at 4400 rpm for 15 min on the next day in order to remove air bubbles. Then, the polymer solution is evenly spread out onto the release liner by means of a doctor blade and the polymer film is dried for 5 h at 40° C. in a drying cabinet. Before testing and further use, the film is cut into appropriately sized pieces and detached from the release liner. The single-layered wafer is stored on the release liner and is wrapped in aluminum foil.

C At first, polyvinyl alcohol (PVA) and Kollicoat IR are dissolved in demineralized water in a beaker at a temperature of 90° C. and at a stirring speed of 400 rpm. Then, Glycerol 85% and the medical substance or the medical substance solution, respectively, are added, homogenized, and the evaporation loss is compensated with demineralized water. The polymer solution is covered and left overnight and is centrifuged at 4400 rpm for 15 min on the next day in order to remove air bubbles. Then, the polymer solution is evenly spread out onto the release liner by means of a doctor blade and the polymer film is dried for 5 h at 40° C. in a drying cabinet. Before testing and further use, the film is cut into appropriately sized pieces and detached from the release liner. The single-layered wafer is stored on the release liner and is wrapped in aluminum foil.

Example 7—Manufacture of Multi-Layered Wafers

For the manufacturing of multi-layered wafers, like those mentioned in Example 3 and Example 4, the individual layers are initially manufactured by the solvent casting method. Therefore, all ingredients of the layer are dissolved in the solvent, homogenized, and subsequently spread out to the desired thickness using a doctor blade. Then, the individual layers are either spread out one above the other or joint together in various ways such as pressure or "gluing". Thereafter, the resulting film is cut into pieces of appropriate size.

In the following, the manufacturing methods for the above-mentioned formulations of two- and three-layered wafers are described in detail:

Manufacture of Two-Layered Wafers:

1 At first, the polymer solution for the mucoadhesive layer containing the active substance is manufactured according to "Manufacture of Single-layered Wafers A" and a 4% (w/v) ethyl cellulose solution EC solution in acetone is prepared. Then, the EC solution is evenly sprayed onto the release liner with the desired layer thickness and dried at room temperature for 15 min. Then, the polymer solution is evenly spread out over it by means of the doctor blade and the resulting two-layered film is dried at 40° C. for 6 h in a drying cabinet. Before testing and further use, the film is cut into appropriately sized pieces and detached from the release liner. The two-layered wafer is stored on the release liner and wrapped into aluminum foil.

2. At first, the polymer solution for the mucoadhesive, active substance containing layer is prepared according to "Manufacture of a Single-layered Wafer A" and a 4% (w/v) EC solution in acetone is prepared. The, the polymer solution is evenly spread out onto the release liner by means of a doctor blade and the polymer film is dried for 4 h at 40° C. in a drying cabinet. Then, the EC solution is evenly sprayed onto the partly dried, still sticky polymer film in the desired layer thickness. Finally, the resulting two-layered film is, again, dried for 2 h at 40° C. in a drying cabinet such that both layers firmly interconnect. Before testing and further use, the film is cut into appropriately sized pieces and pulled off the release liner. The two-layered wafer is stored on the release liner and wrapped in aluminum foil.

3. At first, the polymer solution for the mucoadhesive, active substance containing layer is prepared according to "Manufacture of a Single-layered Wafer A" and a 4% (w/v) EC solution in acetone is prepared. Then, the polymer solution is evenly spread onto the release liner by means of a doctor blade and the polymer film is dried for 4 h at 40° C. in a drying cabinet. In parallel, the EC solution is evenly sprayed onto a second release liner in the desired layer thickness and dried for 15 min at room temperature. Then, the resulting EC film is carefully detached from the release liner and is pressed onto the partly dried, still sticky polymer film by means of a roller. Finally, the now two-layered film is dried for 2 h at 40° C. in a drying cabinet such that both layers firmly interconnect. Before testing and further use, the film is cut into appropriately sized pieces and detached from the release liner. The two-layered wafer is stored on the release liner and wrapped in aluminum foil.

Manufacture of Three-Layered Wafers:

1. At first, the polymer solution for the mucoadhesive, active substance containing layer prepared according to "Manufacture of Single-layered Wafer A", a 4% (w/v) EC solution in acetone, and a 0.5% (w/v) HPMC solution in cold, demineralized water is prepared. Then, the EC solution is evenly sprayed onto the release liner with a desired layer thickness and dried for 15 min at room temperature. Then, the polymer solution is evenly spread out over it by means of a doctor blade and the resulting two-layered film is dried for 6 h at 40° C. in a drying cabinet. Finally, the HPMC solution is spread out over it as a third layer by means of a doctor blade and the resulting three-layered film is, once again, dried for 2 h at 40° C. in a drying cabinet such that all layers firmly interconnect. Before testing and further use, the film is cut into appropriately sized pieces and detached from the release liner. The three-layered wafer is stored on the release liner and wrapped into aluminum foil.

2. At first, the polymer solution for the mucoadhesive layer containing the active ingredient is prepared according to "Manufacture of Single-layered Wafers", a 4% (w/v) EC solution in acetone is prepared, and a 0.5% (w/v) HPMC solution in cold, demineralized water is prepared. Then, the EC solution is evenly sprayed onto the release liner in the desired layer thickness and dried for 15 min at room temperature. Then, the polymer solution is evenly spread out over it by means of a doctor blade and the resulting two-layered film is dried for 6 h at 40° C. in a drying cabinet. In parallel, the HPMC solution is spread out onto a second release liner with their desired layer thickness and dried for 2 h at 40° C. in a drying cabinet. Then, the HPMC film is carefully pulled off the release liner and glued onto the two-layered film with water as binder. Finally, the resulting two-layered film is dried for 1 h at 40° C. in a drying cabinet such that all layers firmly interconnect. Before testing and further use, the film is cut into appropriately sized pieces and pulled off the release liner. The three-layered wafer is stored on the release liner and wrapped into aluminum foil.

3. At first, the polymer solution for the mucoadhesive, active substance containing layer is prepared according to "Manufacture of Single-layered Wafers A", a 4% (w/v) EC solution in acetone is prepared, and a 0.5% (w/v) HPMC solution in cold, demineralized water is prepared. Then, the polymer solution is evenly spread out onto the release liner by means of a doctor blade and the polymer film is dried for 6 h at 40° C. in a drying cabinet. In parallel, the HPMC solution is spread out onto a second release liner in the desired layer thickness and dried for 1 h at 40° C. in a drying cabinet. Then, the resulting polymer film is carefully pulled off the release liner and pressed onto the partly dried, still sticky HPMC film by means of a roller. Then, the now two-layered film is dried for 1 h at 40° C. in a drying cabinet such that both layers firmly interconnect. Finally, the EC solution is evenly sprayed onto the two-layered film with a desired layer thickness and the resulting three-layered film is dried for 30 min at room temperature. Before testing and further use, the film is cut into appropriately sized pieces and pulled from the release liner. The three-layered wafer is stored on the release liner and wrapped into aluminum foil.

4. At first, the polymer solution for the mucoadhesive, active substance containing layer is prepared according to "Manufacture of Single-layered Wafers A", a 4% (w/v) EC solution in acetone is prepared, and a 0.5% (w/v) HPMC solution in cold, demineralized water is prepared. Then, the HPMC solution is spread out onto the release liner with a desired layer thickness and dried for 2 h at 40° C. in a drying cabinet. Then, the polymer solution is spread out over it by means of a doctor blade and the resulting two-layered film is dried for 4 h at 40° C. in a drying cabinet. In parallel, the EC solution is evenly sprayed onto a second release liner in the desired thickness and dried for 15 min at room temperature. Subsequently, resulting EC film is carefully pulled off the release liner and pressed onto the partly dried, still sticky two-layered film by means of a roller. Finally, the now three-layered film is dried for 2 h at 40° C. in a drying cabinet such that all layers firmly interconnect. Before testing and further use, the film is cut into appropriately sized pieces and pulled off the release liner. The three-layered wafer is stored on the release liner and wrapped into aluminum foil.

The features of the present invention disclosed in the description above, in the claims, and in the drawings can be essential both individually and also in any combination for implementing the invention in its various embodiments.

Figure 8:
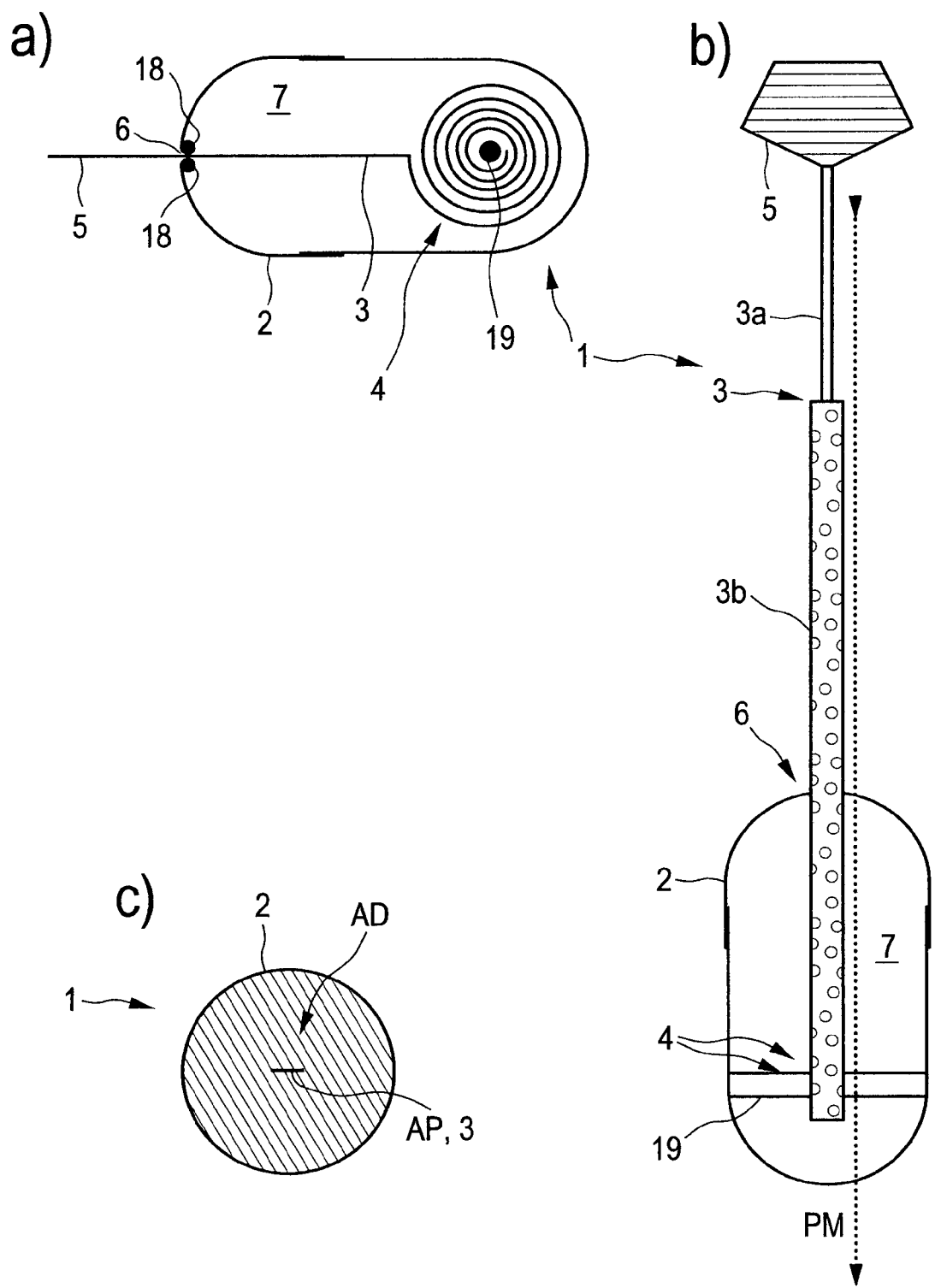
FIG. 8A-C show a schematic illustration of a pharmaceutical dosage form according to the invention in accordance with a fourth embodiment of the invention (FIG. 8A and FIG. 8B) and an illustration of the enveloping cross-sectional areas of the fourth embodiment of the invention.

In FIG. 8a a schematic illustration of the pharmaceutical dosage form 1 according to the invention in accordance with a fourth embodiment of the invention is shown. In particular, this illustration shows the pharmaceutical dosage form 1, wherein the sheet like preparation 3 is in a compact form. Moreover, without limiting the scope of this example, FIG. 8a shows the pharmaceutical dosage form 1 as a side view. A part of the sheet like preparation 3 is a rolled around a rod 19. This roll of the sheet like preparation 3 and the rod 19 together with the elongated part of the sheet like preparation 3 form the release mechanism. It is to be understood, that in some variants of the fourth embodiment the rod 19 is not necessary for the release mechanism 4, and thus omitted. The shell 2 contains the release mechanism 4 in the inner space 7 of the shell 2. Thus, the sheet like preparation 3 and the release mechanism form is protected. Preferably, the shell 2 is formed as a capsule. This capsule 2 facilitates swallowing the dosage form or, in particular, the part of the dosage form that have to be swallowed for the desired application. Furthermore, the shell 2 comprises an aperture 6, through which the sheet like preparation 3 may leave the shell 2. It is to be understood, that also the aperture 6 may be regarded as a part of the release mechanism 4 as it facilitates the release of the sheet like preparation 3. The trigger mechanism 5 is connected to the sheet like preparation 3 and is outside the shell 2. It is to be understood, that a part of the trigger mechanism 5 may be inside the shell 2 and/or that a part of the sheet like preparation 3 may be outside the shell 2. Moreover, the trigger mechanism 5 may be formed by a sophisticated part of the sheet like preparation 3. Additionally, the shell 2 comprises a sealing 18 that seals the aperture 6, at least in an initial state of the dosage form 1, in particular in a state of the dosage 1 that is particularly suited for storage. Such a manner, the inner space of the shell 7 may be protected from the environment such as humidity, liquids or microbes.

Especially, the fourth embodiment relates to an orally administrable dosage form for the treatment of the esophageal mucosa. In this case, it can deliver useful substances such as an active pharmaceutical ingredient to the esophageal mucous membrane by unrolling its sheet like preparation 3 while moving along the esophagus when it is swallowed. Thus, active pharmaceutical ingredients contained in the sheet like preparation 3 can be locally released to the mucous membrane of the esophagus. Current treatments for local diseases of the esophagus generally employ swallowing the content of application systems, which were designed for inhalation therapy of the lung, or swallowing a gel containing specific drugs. However, generally the swallowed content of the application systems or the gel only has a short contact time with the esophageal mucosa. Therefore, the local effect is decreased and the systemic effect is increased, in particular, compared to an application form, in which the contact time is prolonged. By applying the sheet like preparation 3 to the esophageal mucosa a pharmaceutical dosage form 1 according to the fourth embodiment of the invention the treatment of local diseases of the esophagus can be improved and, in particular, the contact time can be prolonged. When applied to the esophageal mucosa, the sheet like preparation 3 stays in contact with the mucosa whilst providing a controlled release of the active pharmaceutical ingredient in order to achieve a local therapy or diagnosis. Preferably, the controlled release can neither be immediate, sustained or prolonged, also preferably, during or after the release of the active pharmaceutical ingredient or the active pharmaceutical ingredients the sheet like preparation 3 dissolves and is, preferably swallowed. Moreover, the shell 2 may detach from the sheet like preparation 3 immediately after the release of the sheet like preparation 3 or may dissolve while still attached to the sheet like preparation 3. Preferably, the shell 2 is made of a dissolvable and/or digestible material. Moreover, the trigger mechanism 5 is a holding device 5. In particular, the holding device 5 is adapted to be fixed in the oral cavity. Therefore, the holding device 5 has a mucoadhesive surface, preferably comprising cellulose derivates, starch and starch derivates, polyvinyl alcohol, polyethylene oxide, polyethylene, polypropylene, polyacrylic acid and polyacrylate derivates, polyvinylpyrrolidone, Povidone, Copovidone, sodium alginate, gelatin, xanthan gum, guar gum, Carrageenan, pectins, dextrans, lectins, Chitosan, Pullulan an mixtures thereof. So, preferably, the holding device 5 can be attached to the oral mucosa, in particular the buccal mucosa, i.e. the inside of the cheek.

Even more specifically, the fourth embodiment of the invention may refer to a pharmaceutical dosage form for the treatment of eosinophilic esophagitis. Eosinophilic esophagitis is an inflammatory, immune-mediated disease with increasing relevance in gastrointestinal disorders. This disease can be treated with topic steroids. Preferably, the shell 2 is a capsule made out of hard gelatin. In an initial state of the dosage form 1, the sheet like preparation 3 is in a compact form, in particular in form of a coil, and is connected to the trigger mechanism 5. The trigger mechanism 5 is a holding device 5 as described above. On administration, the holding device is attached in the oral cavity, preferably to the buccal mucosa, in particular by gluing it to the mucosa. Next, the dosage form 1 is swallowed, preferably with a beverage or water, and, therefore, the dosage form 1 moves along the esophagus and a force acts on the holding device 5 triggering the release of the sheet like preparation 3 by the release mechanism 4. While the dosage form 1 moves down the esophagus the sheet like preparation 3 is unrolled, and thus released. Preferably, the sheet like preparation is mucoadhesive, and thus may adhere to the mucous membrane of the esophagus. In this case, the contact and/or position of the sheet like preparation is not or is not only dependent on the holding device 5. Afterwards, an oblong region of the esophageal mucosa is covered or at least near to the sheet like preparation 3. Thus, it can be treated with active pharmaceutical ingredients, in particular topic steroids, released by the sheet like preparation 3. Preferably, the sheet like preparation 3 may comprise and release fluticasone or budesonide.

Preferably, the manufacture of a sheet like preparation 3, in particular according to the fourth embodiment of the present invention, is carried out by a solvent casting method, wherein at first all ingredients are dissolved in the solvent, homogenized, and subsequently spread out on a suitable release liner to the desired thickness using a doctor blade. Then, the resulting film is dried under defined conditions and then cut into pieces of suitable size.

In a preferred variant, the ingredients, particularly the polymer matrix, consists of 10% m/m polyvinyl alcohol (PVA) (Mowiol 40-88) suspended in a 20% m/m Kollicoat IR aqueous solution. Furthermore, the active pharmaceutical ingredient such as fluticasone or budesonide as well as additives such as methylene blue as a visual control is added.

A sheet like preparation 3 manufactured according to this preferred variant has been experimentally analyzed. For this purpose the sheet like preparation 3 was tested for film thickness and uniformity of mass. Furthermore, disintegration time was tested both and purified water and on wetted are alginate gel (3% m/m) to simulate the mucosa. Fully disintegration was defined as the absence of any solid matrix particle. Tensile strength, elongation and extraction force have been measured using a texture analyzer. All tests were performed triplicate and mean plus/minus standard derivation are reported. The resulting sheet like preparation 3 had a thickness of 114±5 µm and a mean mass of 9.39±0.03 mg/cm$^2$. The disintegration time in water was 760±35 s, and greater than 1200 s on alginate gel. The tensile strength was 31.35 MPa. The elongation at break was 7.41±0.90%.

Preferably, a pharmaceutical dosage form 1, in particular according to the fourth embodiment of the present invention, may be manufactured as described in the following:
cutting the film resulting from a solvent casting technique to strips of 400 mm by 4 mm;
folding or rolling the resultant sheet like preparations 3;
providing a hard gelatin capsule of size 1 is a shell 2;
cutting an aperture 6 into a part of the hard gelatin capsule 2, specifically, as illustrated, into the upper part;
threading one end of the sheet like preparation 3 through the aperture 6; and
closing the capsule 2.

Here, the trigger mechanism, in particular holding device 5, is formed by the part of the sheet like preparation 3 that is outside the shell 2 and the release mechanism 4 is formed by the part of the sheet like preparation 3 that is inside the shell 2, and preferably the aperture 6.

A dosage form 1 manufactured as described above comprising the preferred variant of the sheet like preparation 3, in particular for the fourth embodiment of the present invention, has been experimentally analyzed, as described above. The extraction force of the sheet like preparation 3 from the capsule 2 was 0.31±0.09 N in case of the rolled sheet like preparation 3, and 0.24±0.45 N in case of the folded sheet like preparation 3.

In FIG. 8b a schematic illustration of the pharmaceutical dosage form 1 according to the invention in accordance with the fourth embodiment of the invention is shown. In particular, this illustration shows the pharmaceutical dosage form 1, wherein the sheet like preparation 3 is, at least partially, in an expanded form. Moreover, without limiting the scope of this example, FIG. 8b shows the pharmaceutical dosage form 1 is a top view. The shell 2 contains a rod 19 and a part of the sheet like preparation 3 that is still rolled or coiled, which form the release mechanism 4. The sheet like preparation 3 leaves the shell 2 through the aperture 6. In particular, it is unrolled within the shell 2, i.e. in the inner space of the shell 7, and then elongates into the direction of the aperture 6.

Furthermore, the sheet like preparation 3 is divided into two regions, a first region of the sheet like preparation 3a and a second region of the sheet like preparation 3b. The first region 3a and the second region 3b may comprise different active pharmaceutical ingredients. Preferably, the first region 3a can comprise local anesthetics such as benzocaine, butamben, dibucaine, lidocaine, oxybuprocaine or novocaine, and the second region 3b can comprise a steroid such as corticosteroids, glucocorticoids, fluticasone, budesonide or clocortolone. In particular, in this way, when treating the esophagus, a gag reflex can be suppressed by the local anesthetic and the esophageal mucous membrane can be treated with the steroid. Additionally, the first region 3a has a smaller cross-sectional area than the second region 3b. In particular, this beneficially facilitates swallowing the dosage form.

Furthermore, the holding device 5 is connected to the sheet like preparation 3 or is a broadened part of the sheet like preparation 3 with a mucoadhesive layer preferably comprising: mucoadhesive polymers such as cellulose derivatives, starch and starch derivatives, sodium alginate, gelatin, xanthan gum, guar gum, carrageenan, pectins, dextrans, lectins, and mixtures thereof.

Additionally, the movement path PM of the dosage form 1 is illustrated.

Preferably, the preparation 3 is manufactured according to one manufacturing method described in here. In particular, the sheet like preparation with multiple regions, especially at least a first region 3a and at least a second region 3b, can be manufactured similarly to a multi-layered preparation, wherein, at least some of, the layers are offset to each other but still partially overlap. Also the holding device 5 may be manufactured and/or connected to the sheet like preparation 3 in this way.

FIG. 8c illustrates the enveloping cross-sectional areas of the fourth embodiment of the invention. The pharmaceutical dosage form 1, in particular the shell 2, and the sheet like preparation 3, in particular the portion of the sheet like preparation 3 that just has been released e.g. a portion of the region 3b, are shown as they viewed in the direction of the movement path. Thus, the movement path in FIG. 8c points into the drawing area. As illustrated, the enveloping cross-sectional area of the dosage form AD is larger than the enveloping cross-sectional area of the released part of the sheet like preparation AP. In particular, this facilitates swallowing an orally administrable pharmaceutical dosage form 1.

In particular, the FIGS. 8a, b, and c have the same scale. It is to be understood, that the sheet like preparation 3 may be broader or narrower relative to the capsule 2 than illustrated. Preferably, the sheet like preparation may be broader to better utilize the inner space of the shell 7. Alternatively, the sheet like preparation may be rolled, wherein some windings of the sheet like preparation 3 are beneficially offset to each other. Thus, in particular, the inner space 7 is used in a more efficient way. Also preferably, the sheet like preparation 3 can form or can be comprises by a string member that is rolled or coiled. In particular, such a string member can be coiled in an efficient, reliable and/or space efficient way.

LIST OF REFERENCE SYMBOLS 1 pharmaceutical dosage form
2 shell
3 sheet like preparation
3a, 3b regions of the sheet like preparation, in particular first and second region
4 release mechanism
5 trigger mechanism
6 aperture
7 inner space of the shell
8 predetermined breaking point
9 layer
9a, 9b layer containing an active substance
9c, 9d active substance free layer
10 spring element
11 first tube element
12 further tube element
13 first joint element
14 further joint element
15 central aperture of the wafer balloon
16 slit
17 cladding or shell parts
18 sealing
19 rod
PM movement path
AD enveloping cross-sectional area of the dosage form
AP enveloping cross-sectional area of the released part of the sheet like preparation

The invention claimed is:

1. A pharmaceutical dosage form for the application to an esophageal mucous membrane, comprising a film shaped, foil shaped, wafer shaped or strip shaped preparation comprising an active pharmaceutical ingredient,
a release mechanism; and
a trigger mechanism, wherein
the trigger mechanism is adapted to trigger, at a predetermined site of action, the release of the preparation by the release mechanism, and wherein the release mechanism is adapted to release said preparation while moving along the esophageal mucous membrane, wherein the pharmaceutical dosage form further comprises a shell, wherein the shell contains the preparation, and wherein the shell comprises an aperture as part of the release mechanism configured to allow said preparation to leave the shell, and wherein the trigger mechanism is a holding device that is a part of or is attached to the preparation, and wherein the trigger mechanism is adapted to be fixed in an oral cavity, or wherein the trigger mechanism is adapted to be held in a hand during administration of the pharmaceutical dosage form, such that the preparation is unrolled or unfolded while the dosage form moves down the esophageal mucous membrane and leaves the shell through the aperture.

2. The pharmaceutical dosage form according to claim 1, wherein
the trigger mechanism is adapted to trigger the release of the preparation by the release mechanism after a contact of the pharmaceutical dosage form with a key stimulus or
the trigger mechanism is adapted to trigger the release of the preparation by the release mechanism in a time controlled manner or immediately or
the release mechanism is adapted to release the preparation in a time controlled manner or immediately after triggering of the trigger mechanism.

3. The pharmaceutical dosage form according to claim 1, wherein the preparation further comprises a swelling agent.

4. The pharmaceutical dosage form according to claim 1, wherein: the preparation provides, after its release by the release mechanism, a larger surface area in comparison to the volume of said preparation.

5. The pharmaceutical dosage form according to claim 1, wherein: the release mechanism is an expansion mechanism adapted to expand the preparation by leveraging an external movement, force or pressure.

6. The pharmaceutical dosage form according to claim 1, wherein; the released portion of the preparation and the dosage form move relatively to each other thereby defining a movement path (PM) of the dosage form, and the enveloping cross-sectional area (AD) of the dosage form viewed in the direction of the movement path is larger than the enveloping cross-sectional area (AP) of the released part of the preparation.

7. The pharmaceutical dosage form according to claim 1, wherein said preparation comprises at least one active pharmaceutical ingredient selected from the group consisting of corticosteroids, glucocorticoids, fluticasone, budesonide, clocortolone, perdesonide, hydrocortisone, clobetasonbutyrate, flumetason, flupredniden, hydrocortisone aceponate, hydrocortisone buteprate, hydrocortisone-17-butyrate, triamcinolonacetonid, amcinoid, betamethason-17, 21-dipropionate, betamethason-17-valerate, desoximetasone, diflucortolon-21-valerate, fluocinolonacetonid, fluocinonid, fluticason-17-propionate, methylprednisolone aceponate, mometasone furoate, pednicarbat and clobetasol-17-propionate.

8. The pharmaceutical dosage form according to claim 1, wherein in an initial state of the dosage form, the preparation is in a compact form.

9. The pharmaceutical dosage from according to claim 1, wherein the release mechanism is formed by the part of the preparation that is inside the shell and the aperture.

10. The pharmaceutical dosage from according to claim 9, wherein the shell contains a rod and a part of the preparation is rolled or coiled around the rod and forms together with the elongated part of the preparation the release mechanism.

11. The pharmaceutical dosage form according to claim 1, wherein the holding device is attached in the oral cavity by gluing it to the mucosa.

12. The pharmaceutical dosage form according to claim 1, wherein the preparation comprises muchoadhesive polymers.

13. The pharmaceutical dosage form according to claim 1, wherein the preparation comprises a string member.

* * * * *